(12) United States Patent
Minemura et al.

(10) Patent No.: US 10,006,755 B2
(45) Date of Patent: Jun. 26, 2018

(54) OPTICAL MEASUREMENT APPARATUS AND OPTICAL MEASUREMENT METHOD

(71) Applicant: Hitachi-LG Data Storage, Inc., Tokyo (JP)

(72) Inventors: Hiroyuki Minemura, Tokyo (JP); Kentaro Osawa, Tokyo (JP)

(73) Assignee: Hitachi-LG Data Storage, Inc., Tokyo (JP)

(*) Notice: Subject to any disclaimer, the term of this patent is extended or adjusted under 35 U.S.C. 154(b) by 90 days.

(21) Appl. No.: 14/991,022

(22) Filed: Jan. 8, 2016

(65) Prior Publication Data
US 2016/0265899 A1 Sep. 15, 2016

(30) Foreign Application Priority Data
Mar. 11, 2015 (JP) .................. 2015-047871

(51) Int. Cl.
*G01B 9/02* (2006.01)
*A61B 5/00* (2006.01)

(52) U.S. Cl.
CPC ........ *G01B 9/02091* (2013.01); *A61B 5/0066* (2013.01); *G01B 9/02034* (2013.01); *G01B 9/02038* (2013.01); *G01B 9/02059* (2013.01); *G01B 9/02063* (2013.01); *G01B 9/02064* (2013.01); *G01B 9/02081* (2013.01); *G01B 9/02087* (2013.01)

(58) Field of Classification Search
CPC ............ G01B 9/02034; G01B 9/02038; G01B 9/02059; G01B 9/02063; G01B 9/02064; G01B 9/02081; G01B 9/02087; G01B 9/02091; A61B 5/0066
See application file for complete search history.

(56) References Cited

U.S. PATENT DOCUMENTS

| | | | |
|---|---|---|---|
| 9,383,188 B2 | 7/2016 | Osawa et al. | |
| 9,759,545 B2 | 9/2017 | Mukoh et al. | |
| 2011/0080815 A1* | 4/2011 | Mikami | G11B 7/0065 369/47.19 |
| 2013/0027711 A1 | 1/2013 | Hajian et al. | |
| 2013/0208332 A1 | 8/2013 | Yu et al. | |
| 2014/0023255 A1 | 1/2014 | Lim et al. | |
| 2014/0204388 A1 | 7/2014 | Osawa et al. | |

(Continued)

FOREIGN PATENT DOCUMENTS

| | | |
|---|---|---|
| CN | 100401974 C | 7/2008 |
| CN | 102200593 A | 9/2011 |
| CN | 103852168 A | 6/2014 |

(Continued)

OTHER PUBLICATIONS

Extended European Search Report received in corresponding European Application No. 16154590.0 dated Jul. 29, 2016.

(Continued)

*Primary Examiner* — Michael A Lyons
(74) *Attorney, Agent, or Firm* — Mattingly & Malur, PC

(57) ABSTRACT

By utilizing the fact that the observation object has a three-dimensional shape and the boundary surface can be regarded as a plane surface, phase or intensity distribution is applied into a luminous flux of reference light, thereby selectively attenuating the influence of the reflected light from the boundary surface so as to obtain a high-quality OCT image.

20 Claims, 26 Drawing Sheets

(56) References Cited

U.S. PATENT DOCUMENTS

2016/0054113 A1* 2/2016 Osawa ............... G01B 9/02083
356/497

FOREIGN PATENT DOCUMENTS

| CN | 103961059 A | 8/2014 |
|---|---|---|
| EP | 2 988 092 A1 | 2/2016 |
| JP | 2007-240453 A | 9/2007 |
| JP | 2011-196694 A | 10/2011 |
| WO | 01/42735 A1 | 6/2001 |

OTHER PUBLICATIONS

Zhou, L. et al., "Improvement of axial resolution in optical coherence tomography by optical pupil filter", Optical Sensing II, May 22, 2007, pp. 65342T-1-653421-6, vol. 65342, WA, United States.
Chinese Office Action received in corresponding Chinese Application No. 201610091433.1 dated Feb. 24, 2018.

* cited by examiner

FIG. 5A
FIG. 5B
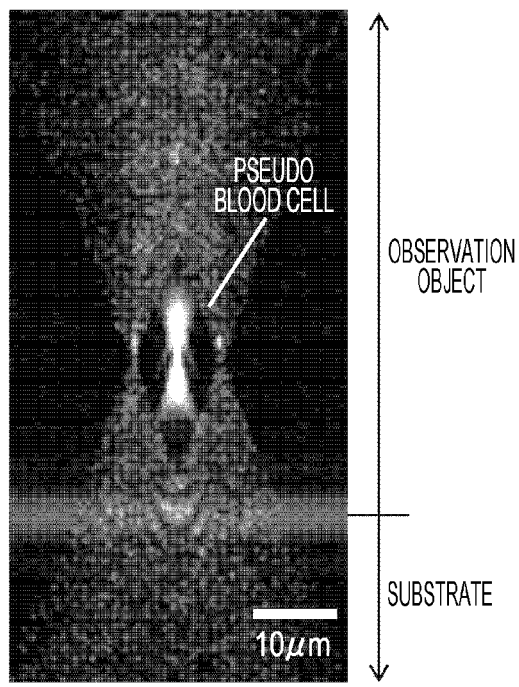
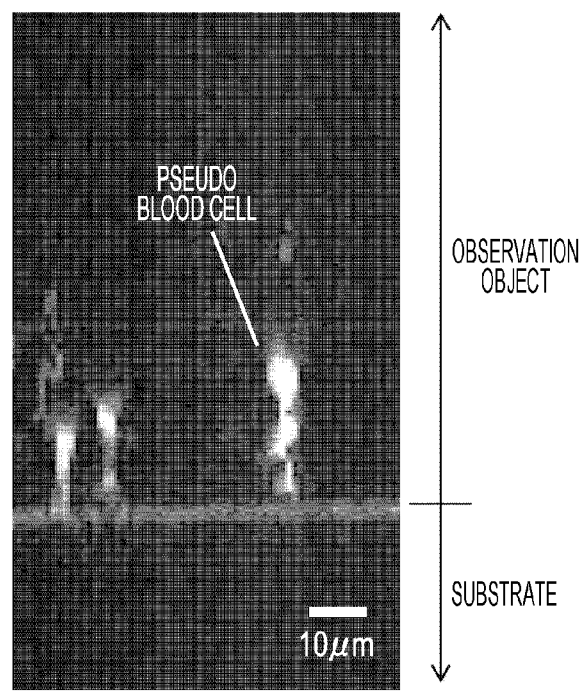

OPTICAL MEASUREMENT APPARATUS AND OPTICAL MEASUREMENT METHOD

CLAIM OF PRIORITY

The present application claims priority from Japanese patent application serial No. JP 2015-047871, filed on Mar. 11, 2015, the content of which is hereby incorporated by reference into this application.

BACKGROUND OF THE INVENTION

1. Field of the Invention

The present invention relates to an optical measurement apparatus. Specifically, the present invention relates to an optical measurement apparatus and an optical measurement method for performing optical tomographic observation.

2. Description of the Related Art

In recent years, attention has been paid to optical coherence tomography (OCT) that obtains an image reflecting a surface structure or an internal structure of an observation object by using light. Since the OCT is non-invasive to a human body, its application to, among others, medical fields and biological fields has been expected. In the ophthalmological field, an apparatus to form an image of a fundus or a cornea has been put in practical use. In the OCT, light from a light source is branched into signal light and reference light. The signal light is obtained by irradiating an observation object with the light from the light source. The reference light is not radiated to the observation object but is reflected by a reference light mirror. The signal light reflected from the observation object and the reference light are combined and interfere with each other, whereby a signal is obtained.

The OCT is roughly classified into time domain OCT and Fourier domain OCT according to a method for scanning a measurement position in an optical axis direction. In the time domain OCT, a low-coherence light source is used as the light source, and the scan in the optical axis direction is performed by scanning the reference light mirror at the time of measurement. As a result, only a component included in the signal light, whose light path length is coincident with that of the reference light, interferes, and a desired signal is demodulated by performing envelope detection on the obtained interference signal. On the other hand, the Fourier domain OCT is further classified into wavelength scanning OCT and spectral domain OCT. In the wavelength scanning OCT, a wavelength scanning light source capable of scanning a wavelength of emitted light is used. The scan in the optical axis direction is performed by scanning the wavelength at the time of measurement. A desired signal is demodulated by performing Fourier transform on wavelength dependence (interference spectrum) of detected interference light intensity. In the spectrum domain OCT, a wide-band light source is used as the light source. Generated interference light is spectrally dispersed by a spectroscope, and interference light intensity (interference spectrum) of each wavelength component is detected, which corresponds to performing the scan in the optical axis direction. A desired signal is demodulated by subjecting the obtained interference spectrum to Fourier transform.

In the OCT, as described above, image information reflecting the internal structure of the observation object can be obtained basically by the signal light and the reference light interfering with each other. "US 2014/0023255" discloses a technique to process a plurality of images obtained by changing a phase of signal light to increase an observable penetration depth. "JP 2011-196694 A" discloses a technique for the Fourier domain OCT to modulate a phase of reference light based on a wavelength of a light source. As a result, intensity of the reference light is substantially adjusted, whereby fine adjustment for a light path length is no longer required. "JP 2007-240453 A" discloses a technique for the time domain OCT to use a plurality of SLDs as well as to change a phase of reference light, thereby obtaining a difference in absorption distribution of an observation object caused by a difference in a wavelength. "WO 2001/42735" discloses a technique for the time domain OCT to use white light and an SLD as a light source. Specifically, the white light and the SLD are switched to each other, whereby resolving power in a depth direction is allowed to be varied. "US 2014/0204388" discloses a technique for the time domain OCT to physically scan an objective lens as well as to receive interference between signal light and interference light by four detectors with different phase conditions. As a result, it is no longer necessary to scan a mirror to adjust a phase of reference light.

SUMMARY OF THE INVENTION

When a living body is measured by OCT, generally, reflected light from the inside of an observation object is considerably smaller than reflected light generated at a boundary between the observation object and a culture vessel or the like. In the OCT, the sum of such reflected light serving as signal light interferes with reference light, whereby image information is obtained. The reflected light generated at the boundary (hereinafter referred to as boundary reflected light) behaves as noise or crosstalk when observing the reflected light from the inside of the observation object. The boundary reflected light is therefore an unnecessary light component that reduces observation accuracy. Such a reduction in the observation accuracy due to the boundary reflected light is generated, for example, at a boundary between a culture vessel made of glass or plastic and a cell sheet under culture, when observing the cell sheet through the vessel. Alternatively, such a reduction is generated at a boundary between air and a skin surface when observing human skin by the OCT.

FIG. 2 is a schematic diagram illustrating measurement of a cell sheet in a transparent culture vessel filled with culture solution. Assuming that a refractive index of the culture solution or cytoplasm is 1.33, and a refractive index of a cell nucleus, which is a particularly big intracellular component, is 1.38, a reflectance of the cell nucleus obtained by Fresnel equations is about 0.034%. On the other hand, assuming that a refractive index of a typical culture vessel is 1.59, a reflectance of a boundary between the culture vessel and the culture solution/cytoplasm is 0.79%. It can be understood, therefore, that unnecessary light with higher intensity by one or more orders of magnitude is generated as the boundary reflected light. Meanwhile, an actual component (e.g. cell nucleus) in a living cell has a three-dimensional structure, a surface shape of which causes the signal light to be reflected widely. Therefore, less than 0.034% of the light reflected by a single cell component is detected as the signal light, resulting in a further increase in the influence of the boundary reflected light.

Hereinafter, as illustrated in the drawing, the description of the present invention will be given based on a unified coordinate system in which an optical axis direction is set as a z axis.

Generally, assuming that complex amplitude of the signal light is $E_{sig}$, and complex amplitude of the reference light is $E_{ref}$, a detection signal S obtained by the OCT can be expressed by the following formula.

[Mathematical formula 1]

$$S = |E_{sig}|^2 |E_{ref}|^2 \cos(\theta_{sig} - \theta_{ref}) \quad (1)$$

In the formula, $\theta_{sig}$ and $\theta_{ref}$ respectively denote a phase based on a light path length of the signal light and a phase based on a light path length of the reference light.

Next, behavior of the boundary reflected light will be quantified. Assuming that a wavelength of a light source is $\lambda$, a numerical aperture of an objective lens is NA, a boundary position between the culture vessel and the observation object is $z=0$, and a focal position of the objective lens is z, as well as considering defocus wavefront aberration included in the signal light, then a detection signal S (z) obtained by performing a phase diversity detection method is expressed by the following formula.

[Mathematical formula 2]

$$S(z) = |E_{sig}|^2 |E_{ref}|^2 \mathrm{sinc}^2\left(\pi \cdot \frac{z}{\lambda} NA^2\right) \quad (2)$$

FIG. 3 is a diagram illustrating a result of calculating the influence of the boundary reflection. In the calculation, based on (Formula 1), assuming that the wavelength of the light source is $\lambda=780$ nm and the numerical aperture of the objective lens is NA=0.52, the detection signal S obtained under a condition that there is no observation object (the vessel is filled only with the culture solution) was calculated by using the above-mentioned each refractive index. A horizontal axis in the drawing represents the focal position z of the objective lens. As illustrated in the drawing, the influence of the boundary reflected light is not limited to the boundary, but spread to an observation area including the living cell according to a sinc function. It can be understood that significant crosstalk is generated for a reflected signal from the living cell. Unless otherwise noted, the following description will be given based on a unified wavelength of the light source, namely 780 nm, and a unified numerical aperture of the objective lens, namely 0.52.

The techniques disclosed in "US 2014/0023255", "JP 2011-196694 A", "JP 2007-240453 A", "WO 2001/42735" and "US 2014/0204388" have disclosed the techniques to change the phase based on the light path lengths of the signal light and the reference light. However, since the detection signal is obtained in accordance with an amount of the reflected light from the observation object, the influence of the boundary reflected light, which has been pointed out herein, could not have been reduced.

In order to solve the above-mentioned problem, the present invention, paying attention to the fact that a boundary can be approximated to a plane surface while an observation object has a three-dimensional shape, provides an optical measurement method and apparatus capable of selectively attenuating or removing boundary reflected light by applying, to reference light, phase distribution in a direction orthogonal to an optical axis.

The following description of the present invention will refer to a case where a detection signal is obtained by a so-called phase diversity detection method described in "US 2014/0204388" for simplifying the explanation. The technique according to an embodiment of the present invention, however, can be easily expanded to other detection methods by considering a phase based on a light path difference between reference light and signal light.

An OCT apparatus is provided with an optical system in which signal light and reference light combined with each other are collected by a detection lens into an optical detector. As described above, assuming that an optical axis direction is set as a z axis, an aperture of the detection lens is formed on an x-y plane surface. Assuming that a z coordinate of a focus of an objective lens is z, and a z coordinate of the detection lens is $z_0$, as well as formulating interference between the signal light and the reference light as superposition of the interference at each point (x, y, $z_0$) on the aperture of the detection lens, then a detection signal S can be expressed by the following formula.

[Mathematical formula 3]

$$S = \left| \int\int_A E_{sig}(x, y, z_0) \cdot E_{ref}(x, y, z_0) dx dy \right|^2 \quad (3)$$

Expression of (Formula 3) is generalized so as to deal with spatial distribution of the signal light and spatial distribution of the reference light at the aperture of the detection lens. In the techniques of "US 2014/0023255", "JP 2011-196694 A", "JP 2007-240453 A", "WO 2001/42735" and "US 2014/0204388", since reference light is a plane wave and only considers a phase based on a light path length, reference light expressed by the following formula is used, assuming that amplitude A and a light path length L are constants, and i is an imaginary unit.

[Mathematical formula 4]

$$E_{ref}(x, y, z_0) = A \exp\left(i \frac{2\pi}{\lambda} L\right) \quad (4)$$

In the formula, $(2\pi/\lambda) L$ is the phase based on the light path length of the reference light.

The signal light is expressed by the following formula as the sum of the boundary reflected light and reflected light from a plurality of living cells.

[Mathematical formula 5]

$$E_{sig}(x, y, z_0) = E_b \exp\left\{i \frac{2\pi}{\lambda}\left(\frac{x^2 + y^2}{R^2} NA^2 z + L\right)\right\} + \sum_n E_n(x, y, z_0) \quad (5)$$

In the formula, the first term on the right side represents planar boundary reflected light taking defocus wavefront aberration into consideration. $E_b$ is an amplitude reflectance, and R is a radius of the aperture of the detection lens. The second term on the right side represents the sum of the reflected light from each tissue within the living body. Since each tissue has a three-dimensional shape, the reflected light from each tissue within the living body is a wave that has more wavenumber components than the boundary reflected light has. L=0 can be applied to (Formula 4) and (Formula 5) when the phase diversity detection method is used for the detection. In this case, when the second term on the right side of (Formula 5) is zero, (Formula 4) and (Formula 5) are assigned to (Formula 3). $E_b$ is then rewritten to $E_{sig}$, and (Formula 3) can be simplified to match (Formula 2).

Returning to (Formula 3), the inside of the integral is now examined. As a result, it can be understood that a correlation coefficient between the signal light and the reference light is obtained by the inside of the integral. In other words, when the plane wave is used as the reference light in the same way as the conventional OCT represented by "US 2014/0023255", "JP 2011-196694 A", "JP 2007-240453 A", "WO 2001/42735" and "US 2014/0204388", it can be said that the detection signal is obtained by extracting only a plane wave component included in the signal light. Meanwhile, since the observation object, namely the living cell has a three-dimensional solid shape, the reflected light includes not only a reflected component from a plane surface perpendicular to the optical axis but also a component equivalent to reflection from a plurality of plane surfaces inclining relative to the optical axis. In other words, when the plane wave is used as the reference light, a portion of the reflected light from the living tissue is extracted and detected. Therefore, it can be understood, in a case where the boundary can be approximated to the plane surface perpendicular to the optical axis, that the influence of the boundary reflection might be reduced by applying the phase distribution into a luminous flux of the reference light so that correlation with the reflected light from the boundary becomes small.

When considering the phase distribution to be applied into the luminous flux of the reference light, in other words, when appropriately controlling a wavefront of the reference light, a method for numerically solving (Formula 3) is required for examining a specific shape of the wavefront. In this regard, a simulation method based on a ray tracing method extended from a Monte Carlo method has been developed as the result of the following consideration: (1) a representative size of the living cell with the three-dimensional shape ranges from about 10 to 30 µm; (2) a laser or an SLD having a wavelength ranging from visible to near infrared is used as a light source; and (3) calculation time should be as short as possible. Basically, (Formula 3) can be numerically solved at the aperture of the detection lens by calculating information that accompanies each ray. Such information includes phase information according to the light path length and intensity information according to the amplitude, as well as position and speed information. In this method, an amplitude reflectance and transmittance are calculated depending on a change in a ray vector caused by refraction at an object surface, and on an incident angle and polarization according to a Fresnel's law. Hereinafter, this method will be referred to as a wave ray tracing method.

In order to verify calculation accuracy of the wave ray tracing method, an OCT apparatus which has the same optical system (wavelength: 780 nm, numerical aperture of objective lens: 0.52) as that of FIGS. 4A and 4B in "US 2014/0204388" was prepared. Two kinds of specimens using commercially-available pseudo blood cells (refractive index: about 1.59) made of polystyrene were also prepared as measurement samples. The pseudo blood cell and the above-mentioned cell nucleus are different in refractive index but equivalent in size. The reference light is the plane wave having no phase distribution within the luminous flux.

FIGS. 4A and 4B are a comparison between a simulation result and a measurement result by the OCT apparatus with respect to an X-Y image. In the verification, water and single-layered pseudo blood cells were dispersed between a glass substrate and cover glass, and used as a specimen. The simulation was conducted under conditions in which the pseudo blood cell was treated as a spherical body with a diameter of 10 µm, and thirteen pseudo blood cells were regularly arranged. Intensity of the detection signal was calculated by changing the focal position of the objective lens according to mesh points arranged at 0.5 µm intervals throughout an area of 100×100 µm. The result of such calculation is illustrated in the drawing. The number of rays used for the calculation at each mesh point is one million. As illustrated in the drawing, it can be understood that the calculation result and the experiment result are substantially coincident with each other.

FIGS. 5A and 5B are a comparison between a simulation result and a measurement result by the OCT apparatus with respect to an X-Z image. In the verification, a UV resin (refractive index: 1.51) layer with a thickness of about 100 µm, in which the pseudo blood cells were dispersed at a volume fraction of 10%, was formed on a glass substrate, and used as a specimen. The observation result was obtained by radiating laser light from a substrate side in the drawing. The simulation was conducted under conditions in which a single pseudo blood cell was arranged with a distance of 10 µm from an interface of the glass substrate. Calculation was conducted by changing the focal position of the objective lens according to mesh points arranged at 0.5 µm intervals throughout an area of 40×80 µm. The result of such calculation is illustrated in the drawing. As illustrated in the drawing, it can be understood that the calculation result and the experiment result are substantially coincident with each other.

From the results illustrated in FIGS. 4 and 5, and considering an influence caused by variations in size of the pseudo blood cell and a gap between a plane surface to be scanned and a center of the pseudo blood cell, it can be said, in relation to the OCT measurement of the cell component (e.g. cell nucleus) which is bigger than the wavelength, that analysis with necessary and sufficient accuracy can be performed by the wave ray tracing method.

FIG. 6 is an exemplary simulation result that indicates amplitude distribution of the signal light at the aperture of the detection lens. In the simulation, a single spherical body imitating the pseudo blood cell was arranged in the culture solution (refractive index: 1.33), and the focus of the objective lens was shifted from the center of the spherical body in the x direction. An absolute value of a real part of the signal light was then represented as contrast information. In a case where the laser light is radiated to the observation object, namely the spherical body from a lower side thereof, the signal light reflected at a lower hemisphere of the spherical body has a single reflection history. On the other hand, the signal light reflected at an upper hemisphere of the spherical body has two transmission histories and two refraction histories as well as a single reflection history. Therefore, the signal light reflected at the lower hemisphere of the spherical body and that reflected at the upper hemisphere of the spherical body can be separated as different waves. As illustrated in the drawing, the signal light reflected at the upper surface of the spherical body and that reflected at the lower surface of the spherical body have different amplitude distribution according to a curvature of the object surface. Considering that the objective lens has a finite diameter, it can be understood that the detected light is a portion of the reflected signal light, and so-called vignetting is generated. Intervals of the contrast in the drawing indicate that the phase within the aperture (within the luminous flux) is shifted by a ½ wavelength. It is well known that the signal light reflected by a planer object has, at the aperture of the detection lens, constant amplitude and rotationally symmetric phase distribution according to defocus wavefront aberration. It can be understood, therefore, that the signal light reflected by a spherical observation object has obviously different phase distribution within the aperture (within the luminous flux). It is also well known that the actual observation objects, namely the living cell and the internal component structure have a more complex three-dimensional shape. Based on the above-mentioned discussion, therefore, the influence of the boundary reflected light can be reduced by applying the phase distribution into the luminous flux of the reference light, which is because only the phase distribution within the aperture of the detection lens contributes to quality improvement in the detection signal.

As an example of the phase distribution within the luminous flux of the reference light which is effective in reducing the influence of the boundary reflected light, conical phase distribution proportional to a radius of the detection lens was used in a simulation of the detection signal based on the boundary reflected light, the result of which is illustrated in FIG. 7. The conical phase distribution is expressed by the following formula obtained by expanding (Formula 4).

[Mathematical formula 6]

$$E_{ref}(x, y, z_0) = A \exp\left(i\Phi_0 \frac{\sqrt{x^2 + y^2}}{R}\right) \exp\left(i\frac{2\pi}{\lambda}L\right) \quad (6)$$

In the formula, $\varphi_0$ is a maximum value of a phase to be applied, and R is a radius of the aperture of the detection lens. The simulation result in the drawing is a comparison between $\varphi_0=0$ (plane wave) and $\varphi_0=4\pi$ (conical phase distribution). As illustrated in the drawing, it can be understood that, by using the conical phase distribution as the phase distribution within the luminous flux of the reference light, the detection signal by the boundary reflected light is shifted by a certain amount to the opposite side of the observation object area represented by z>0, and amplitude of a periodic change in the intensity of the detection signal, which has been based on a sinc function, is decreased. A simulation that models the living cell was also conducted to generate an x-z image, the result of which will be described in Example.

The results illustrated in FIGS. 6 and 7 have successfully demonstrated that the influence of the boundary reflected light can be reduced by appropriately selecting the phase distribution to be applied into the luminous flux of the reference light.

An embodiment of the present invention can provide an optical measurement method and apparatus capable of observing a living tissue with high accuracy by reducing an influence of boundary reflection that occurs at a boundary, when regarding the living tissue as an observation object, between the observation object and a substrate or a culture case that supports the observation object, or at a boundary between air and a human body. Problems, configurations, and effects other than those mentioned above will be clarified in the following description of the embodiment.

Meanwhile, a technique to modulate a phase of reference light has also been disclosed in "US 2014/0023255", "JP 2011-196694 A", "JP 2007-240453 A", "WO 2001/42735" and "US 2014/0204388". The phase in this regard, however, is a phase based on a light path length in the optical axis direction represented in (Formula 4). It should be noted, therefore, that a phase of reference light disclosed in an embodiment of the present invention mainly means phase distribution within a luminous flux as represented in (Formula 3) and (Formula 6).

BRIEF DESCRIPTION OF THE DRAWINGS

FIGS. 5A and 5B are diagrams comparing a simulation result and a measurement result by the OCT apparatus with respect to an X-Z image;

DESCRIPTION OF THE PREFERRED EMBODIMENTS

Hereinafter, an embodiment of the present invention will be described referring to the accompanying drawings.

Example 1

Figure 6:
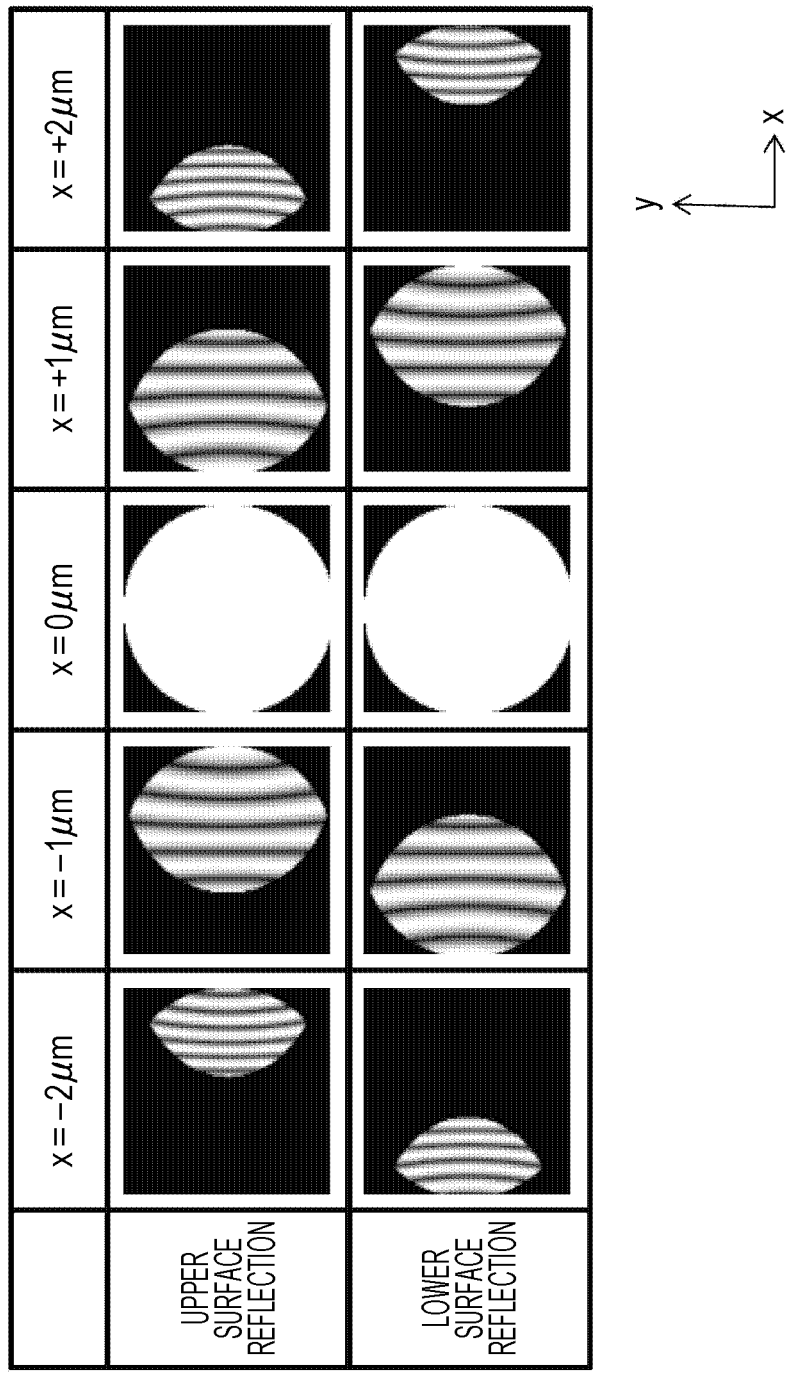
FIG. 6 is an exemplary simulation result that indicates amplitude distribution of the signal light at an aperture of a detection lens.
Figure 7:
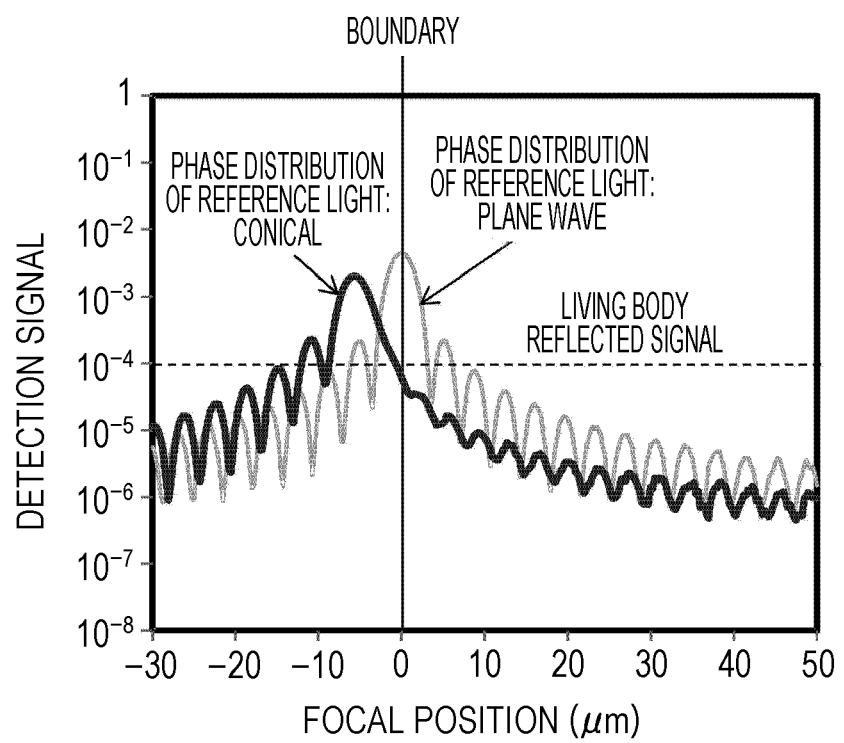
FIG. 7 is a simulation result of the detection signal based on the boundary reflection by reference light with conical phase distribution and plane wave reference light.
Figure 8A:
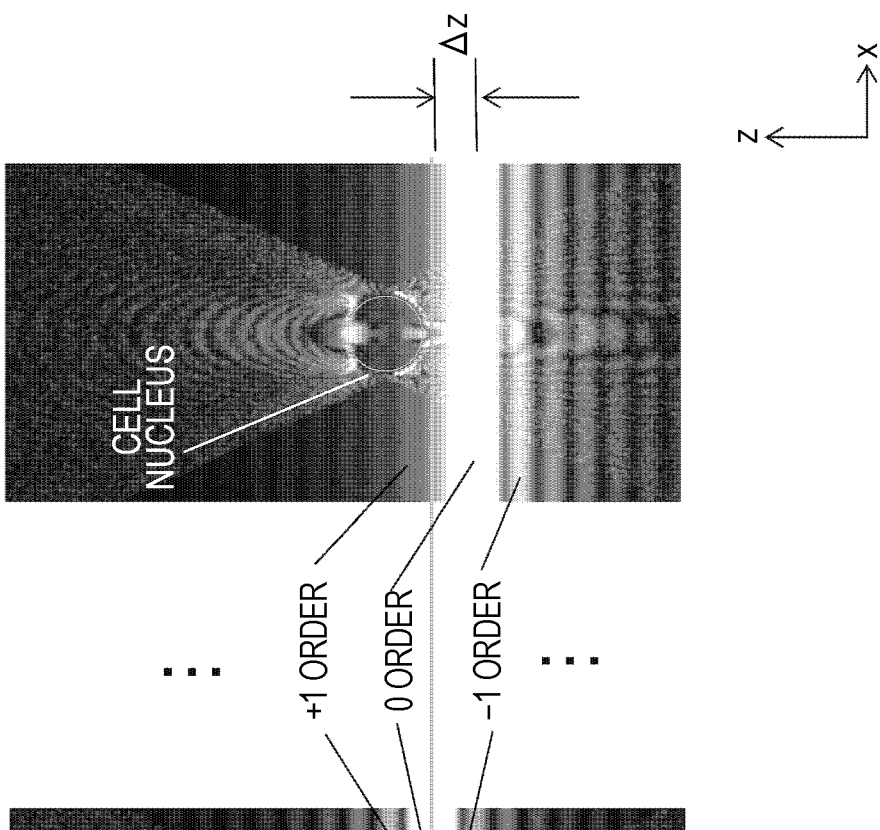
FIGS. 8A and 8B are simulation results comparing an x-z image by the reference light with the conical phase distribution and that by the plane wave reference light.
Figure 8B:
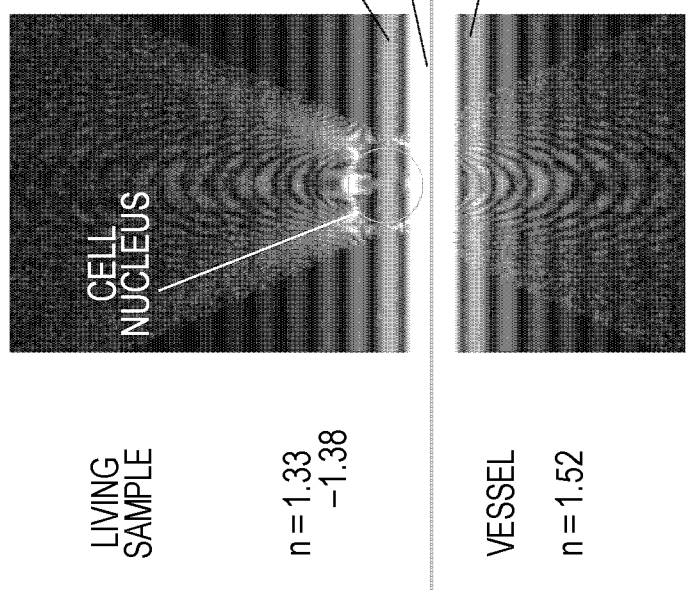

FIGS. 8A and 8B are simulation results comparing an x-z image by reference light with conical phase distribution according to an embodiment of the present invention and that by conventional plane wave reference light. In the simulation, the inside of a culture vessel (refractive index: 1.59) was filled with culture solution (refractive index: 1.33). A spherical body (refractive index: 1.37) with a diameter of 10 μm imitating a cell nucleus was arranged so as to come into contact with a bottom surface of the culture vessel, thereby modeling a living cell. A simulation by a wave ray tracing method was performed on such a living cell model, thereby calculating and imaging a detection signal obtained by scanning a focal position of an objective lens in the x-z direction. A gain of the image has been normalized so that the detection signal corresponding to a reflectance of 0.05% has a maximum luminance level of 255. FIG. 8A is the result of using the plane wave as the reference light. Regarding a pseudo blood cell illustrated in FIGS. 5A and 5B, a spherical body has a large refractive index of 1.59. An influence of boundary reflection is therefore relatively small. Regarding the imitation of the living cell, however, the spherical body modeling the cell nucleus has a refractive index of 1.37, and the culture solution has a refractive index of 1.33. A difference between both refractive indexes is therefore small, from which it can be understood that the influence of the boundary reflection becomes larger. As illustrated in the drawing, the influence of the boundary reflection, reflecting the result illustrated in (Formula 2), repeats vibration according to a sinc function. It can be understood, therefore, that the influence of the boundary reflection is significant crosstalk for the detection signal obtained by the spherical body imitating the observation object, namely the cell nucleus. On the other hand, FIG. 8B is the result of applying the conical phase distribution represented in (Formula 6) into a luminous flux of the reference light. A maximum value of a phase to be applied is the same as the above-mentioned condition, namely $\varphi_0 = 4\pi$. The influence of the boundary reflected light, reflecting the result illustrated in FIG. 7, is shifted to the lower side of the actual boundary position. The vibration of intensity due to the sinc function in the observation object, namely the living cell area is also decreased. It can be understood, therefore, that the detection signal by the reflected light from the spherical body modeling the cell nucleus becomes clearer. Another important result is that magnitude of the detection signal based on the reflected light from the spherical body modeling the cell nucleus is substantially constant since FIGS. 8A and 8B are normalized to the same gain. This result is obtained because the reflected light reflecting a three-dimensional shape of the observation object has the different phase distribution from that of plane reflection as illustrated in FIG. 6. Another reason for this result is that the detection signal is an optical operation that correlates the reflected light (signal light) and the reference light as represented in (Formula 3). It has been proved that, according to an embodiment of the present invention, accuracy of the observation result can be improved by reducing intensity attenuation in the detection signal from the reflected light of the living cell nucleus, as well as by selectively attenuating the influence of the boundary reflection, when appropriately selecting a value of the phase distribution to be applied into the luminous flux, even when the reference light is not the plane wave.

Figure 9:
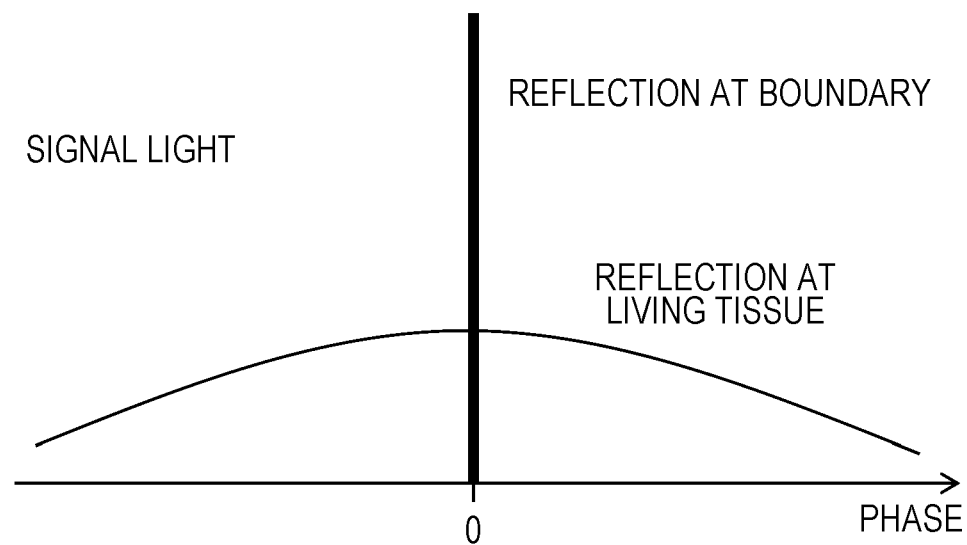
FIG. 9 is a schematic diagram illustrating a spectrum of a phase component included in reflected light.
Figure 9:
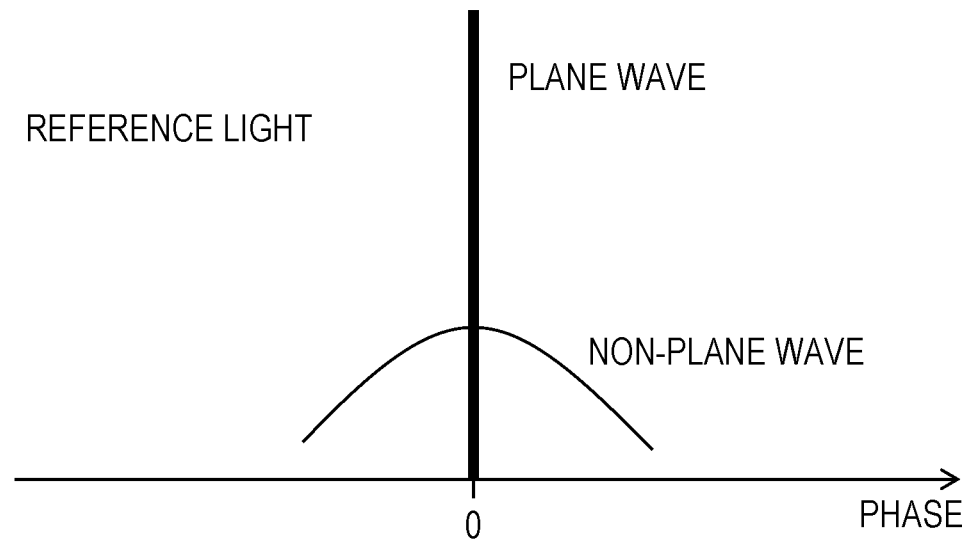

FIG. 9 is a schematic diagram illustrating a spectrum of a phase component included in the reflected light. In a case where the objective lens is focused on a boundary surface, the reflected light from the boundary is formed into the plane wave at an aperture of a detection lens as illustrated in the drawing, whereby the phase is not distributed within the x-y surface. On the other hand, since a living tissue has a three-dimensional structure, the phase distribution is widened. Therefore, in a case where the reference light is not the plane wave, the influence of the boundary reflection included in the detection signal can be selectively reduced.

Figure 10:
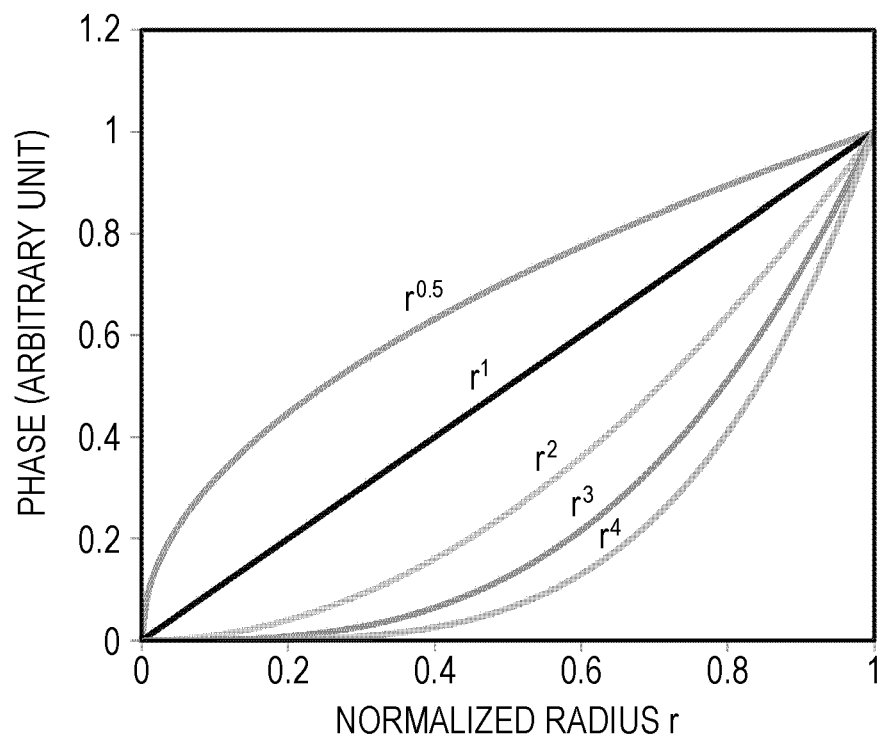
FIG. 10 is a schematic diagram illustrating a plurality of reference light beams with phase distribution dependent on a radius of the detection lens.

FIG. 10 is a schematic diagram illustrating a plurality of reference light beams with phase distribution dependent on a radius of the detection lens. Assuming that the phase distribution within the luminous flux of the reference light is a function of the radius of the aperture of the detection lens, the phase distribution can be applied in the following forms.

[Mathematical formula 7]

$$E_{ref}(x, y, z_0) = A\exp(i\Phi_0 r^a)\exp\left(i\frac{2\pi}{\lambda}L\right) \quad (7)$$

[Mathematical formula 8]

$$r = \frac{\sqrt{x^2 + y^2}}{R} \quad (8)$$

In the formulas, a normalized radius r is defined by (Formula 8) and determined by a position (x, y) within the aperture of the detection lens and a radius R of the aperture of the detection lens. (Formula 7) is obtained by generalizing (Formula 6) using the normalized radius r. When a degree a=0 is set, the reference light is the plane wave. When a=1 is set, the reference light is formed into the above-mentioned conical shape. As illustrated in the drawing, a=0.5, 1, 2, 3, and 4 are each set to be examined below.

FIGS. 11A to 11F are simulation results of the detection signal based on the boundary reflection by the plurality of reference light beams with the phase distribution dependent on the radius of the detection lens.

Figure 11A:
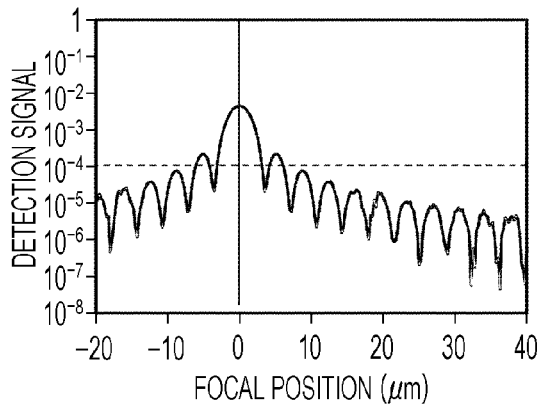
FIGS. 11A to 11F are simulation results of the detection signal based on the boundary reflection by the plurality of reference light beams with the phase distribution dependent on the radius of the detection lens.
Figure 11D:
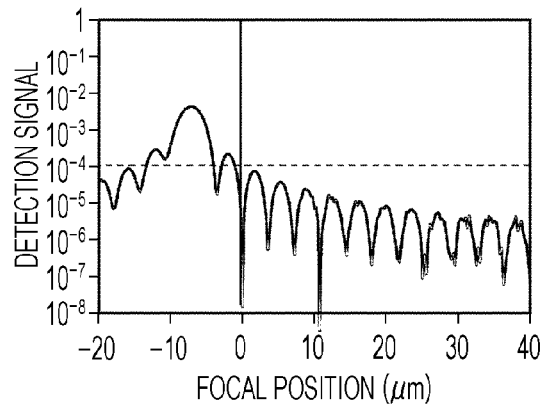
Figure 11B:
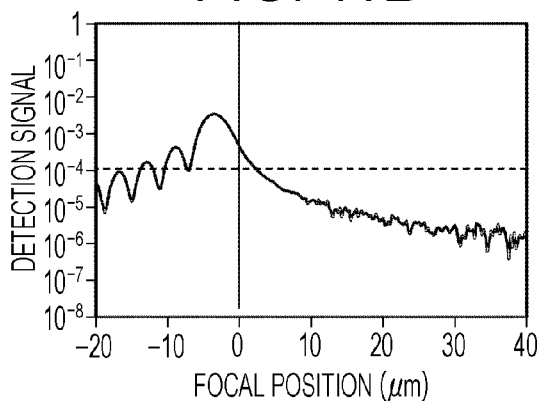
Figure 11E:
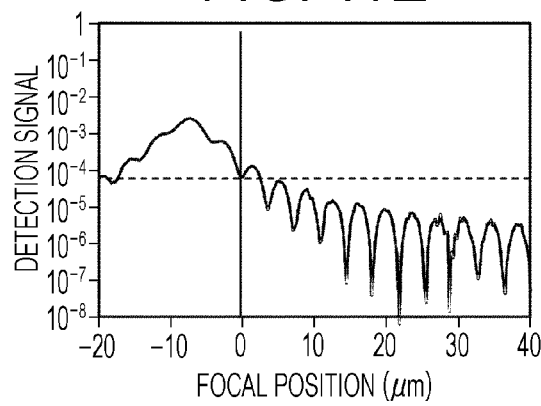
Figure 11C:
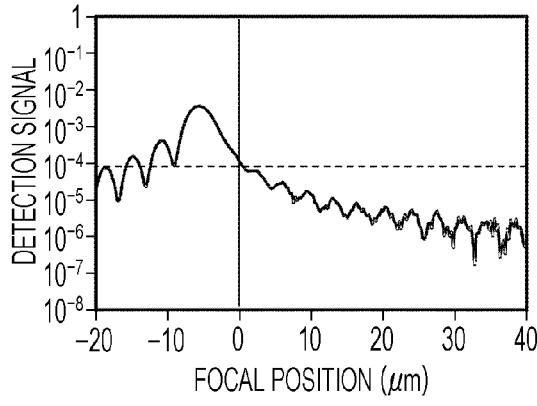
Figure 11F:
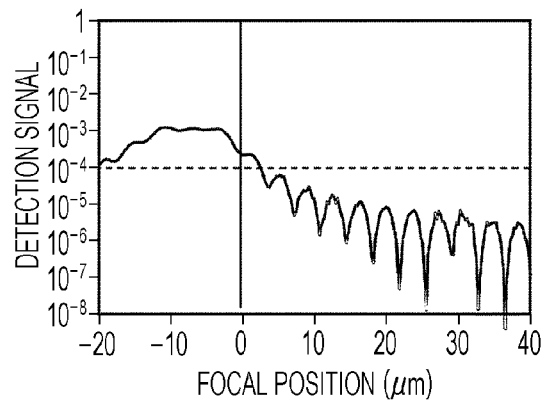

This is a schematic diagram illustrating the plurality of reference light beams with the phase distribution dependent on the radius of a result detection lens. Assuming that the phase distribution within the luminous flux of the reference light is a function of the radius of the aperture of the detection lens, the phase distribution can be applied in the following forms. FIG. 11A represents a=0 (plane wave), FIG. 11B represents a=0.5, FIG. 11C represents a=1 (conical reference light), FIG. 11D represents a=2 (defocus wavefront aberration reference light), FIG. 11E represents a=3, and FIG. 11F represents a=4. A simulation condition is constant at $\varphi_0=4\pi$ in the same way as the result illustrated in FIG. 7. A combination of FIGS. 11A and 11C coincides with FIG. 7. Focusing on the vibration based on the sinc function in a living specimen area of z>0, when the degree a=0.5, 1 is set, vibration amplitude of the detection signal is obviously smaller than that when a=0 (plane wave) is set. It can be understood that a vibration component of the observed image can be advantageously reduced. Focusing then on a peak value of the detection signal, when the degree a=3, 4 is set, a peak of the detection signal is obviously smaller and has a flatter shape than that when a=0 (plane wave) is set. It can be understood that an occurrence condition of output saturation in an optical detector can be advantageously moderated, and a favorable condition in terms of S/N ratio for amplifier noise or circuit noise can be advantageously obtained.

Figure 12:
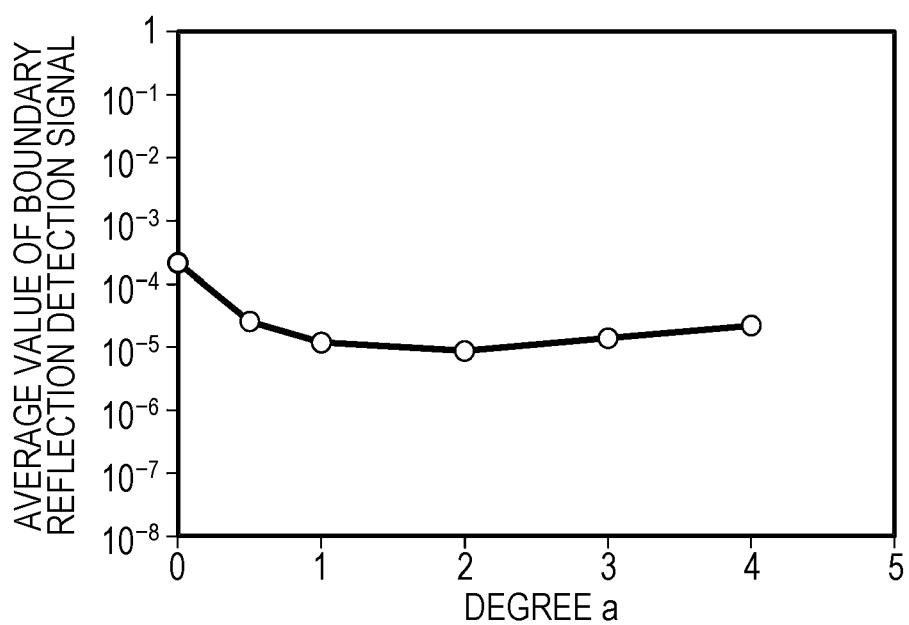
FIG. 12 is a simulation result illustrating a relation between a degree of the radius and an average value of the detection signal based on the boundary reflection by the reference light having rotationally symmetric phase distribution within a luminous flux.

FIG. 12 is a result of summarizing the results of FIGS. 11A to 11F in terms of a relation between the degree a and an average value of the detection signal based on the boundary reflection in the living specimen area (z>0). It can be understood from the drawing that the average values in the living specimen area when the reference light according to an embodiment of the present invention (a>0) is used are smaller than the average value in the living specimen area when the conventional plane wave reference light (a=0) is used. It can also be understood that the influence of the boundary reflection is reduced when the reference light according to an embodiment of the present invention is used. As illustrated in the drawing, a minimum value of the average value is in a range from a=0 to a=1. It can be understood, therefore, that quality of the detection signal based on the boundary reflection can be advantageously improved.

Figure 13A:
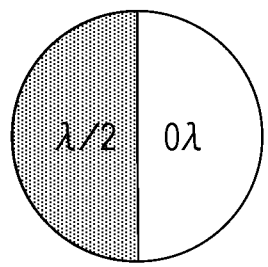
FIGS. 13A to 13D are schematic diagrams illustrating the reference light having step-like phase distribution within the luminous flux.
Figure 13B:
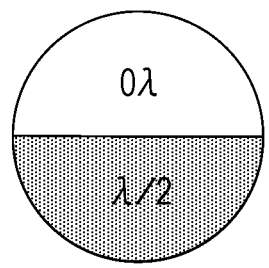
Figure 13C:
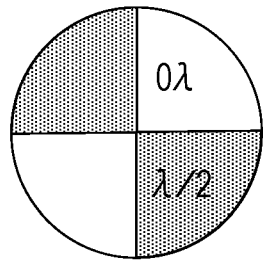
Figure 13D:
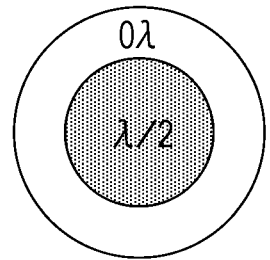
Figure 13D:
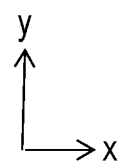

In the optical measurement method according to an embodiment of the present invention in which the phase distribution is applied into the luminous flux of the reference light, other forms of the phase distribution can also be applied. FIGS. 13A to 13D are schematic diagrams illustrating the reference light having step-like phase distribution within the luminous flux. An area to which a phase difference of $\lambda/2$ (+$\pi$) is applied within the luminous flux of the reference light is indicated by a hatched area in the drawing. In FIG. 13A, it is illustrated that the luminous flux is divided into two in the x direction, and the phase difference is applied to the left side. The form of FIG. 13A has a characteristic that, for example, the phase distribution of the reference light on the aperture of the detection lens does not change even by scanning the objective lens in the y direction. In FIG. 13B, it is illustrated that the luminous flux is divided into two in the y direction, and the phase difference is applied to the lower side. The form of FIG. 13B has a characteristic that, for example, the phase distribution of the reference light on the aperture of the detection lens does not change even by scanning the objective lens in the x direction. In FIG. 13C, it is illustrated that the luminous flux is divided into four in the x and y directions, and the phase difference is applied to the lower right and upper left areas. The form of FIG. 13C has a characteristic that, for example, the phase distribution of the reference light on the aperture of the detection lens does not change even by scanning the objective lens in each x and y direction. In FIG. 13D, it is illustrated that the luminous flux is divided into two areas, namely an inner peripheral side and an outer peripheral side, and the phase difference is applied to the inner peripheral side area. It is also illustrated that the applied phase distribution is the same as that of well-known optical super-resolution. Since a component of the optical super-resolution included in the signal light can be extracted by correlation integral according to (Formula 3), the form of FIG. 13D has a characteristic that resolution in the x and y directions can be improved. As indicated in (Formula 2) representing the boundary reflected light, the boundary reflected light is basically a function of only the radius within the aperture of the detection lens, and has rotationally symmetric phase distribution. In the step-like phase distribution illustrated herein, an area in which the phase applied within the aperture of the detection lens is zero (complex amplitude+1) and an area in which the phase applied within the aperture of the detection lens is $\lambda/2$ (complex amplitude−1) are substantially equal in size. Therefore, based on (Formula 3), the detection signal of the reflected light from the plane surface including the boundary reflection becomes zero.

Figure 14B:
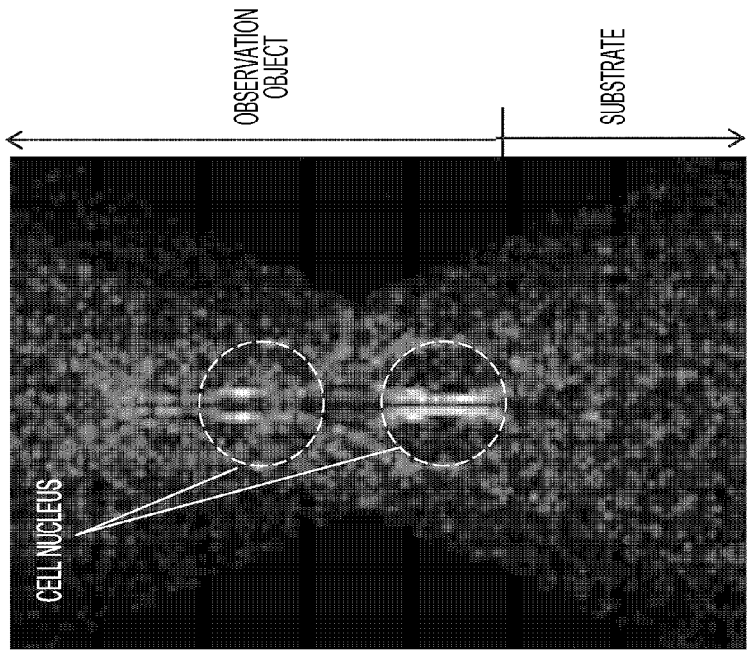
FIGS. 14A and 14B are simulation results illustrating a difference between an x-z image by the reference light having the step-like phase distribution within the luminous flux and that by the plane wave reference light.
Figure 14A:
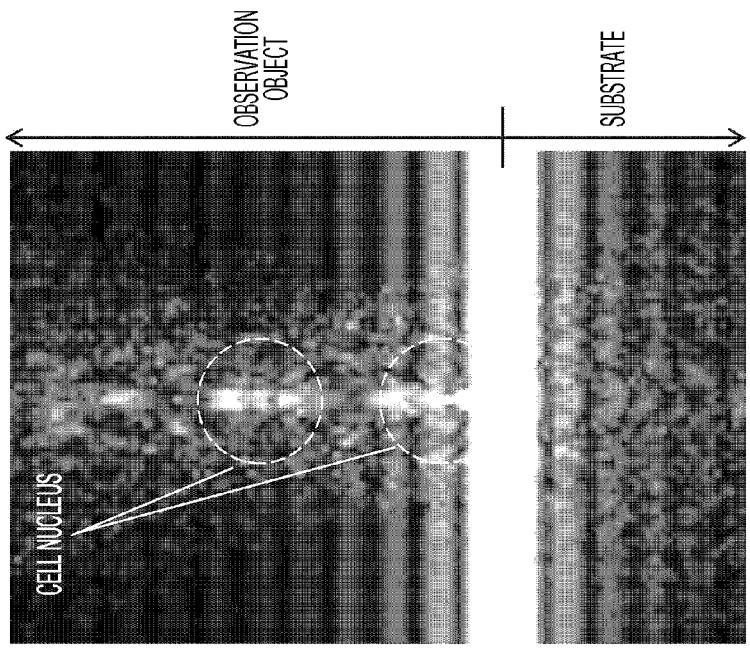

FIGS. 14A and 14B are simulation results comparing an x-z image by the reference light having the step-like phase distribution according to an embodiment of the present invention and that by the conventional plane wave reference light. A simulation condition is generally the same as that illustrated in FIGS. 8A and 8B. The result illustrated herein was obtained by arranging two spherical bodies in the z direction, each with a diameter of 10 μm and imitating the cell nucleus. FIG. 14A is the x-z image obtained by the conventional plane wave reference light. It can be understood that the influence of the boundary reflected light causes significant crosstalk for the detection signal from the two spherical bodies imitating the living nucleuses to be observed. FIG. 14B is the x-z image obtained by using the reference light having the step-like phase distribution illustrated in FIG. 13C within the luminous flux. As mentioned above, it can be understood that the boundary reflected light completely reaches zero, and the detection signal based on the reflected light from the two spherical bodies can be obtained as an image. The image of FIG. 14B is dark at a central axis of the two spherical bodies, which is caused by the fact that this reference light causes the detection signal to reach zero when complex amplitude distribution of the signal light is symmetrically applied with respect to a lens center within the aperture of the detection lens. In terms of the reduction in the influence of the boundary reflection, the step-like phase distribution within the luminous flux of the reference light described herein is superior to the phase distribution dependent on the radius based on (Formula 7). The step-like phase distribution is disadvantageous, however, in that the detection signal from a central part of the observation object is small when the observation object has a symmetrical shape like the spherical body. Since the actual living cell component has an asymmetrical structure rather than the perfect spherical body described herein, the reduction in the detection signal from the central part is expected to be moderated. In the optical measurement method according to an embodiment of the present invention, however, it is important to appropriately select the phase distribution to be applied into the luminous flux of the reference light according to the observation object taking these characteristics into consideration.

Figure 15A:
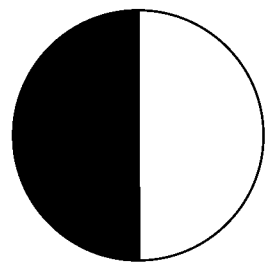
FIGS. 15A to 15E are schematic diagrams illustrating the reference light having step-like intensity distribution within the luminous flux.
Figure 15B:
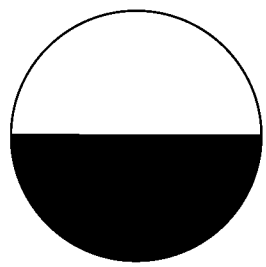
Figure 15C:
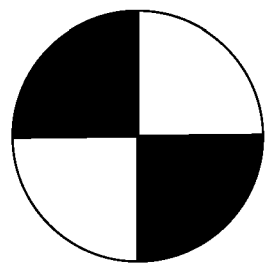
Figure 15D:
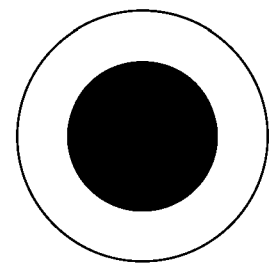
Figure 15E:
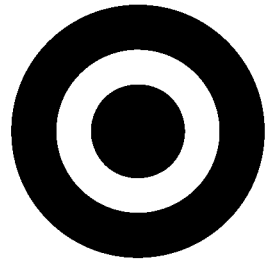
Figure 15E:
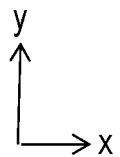

The optical measurement method according to an embodiment of the present invention, in which specific phase distribution is applied into the luminous flux of the reference light, has been described above. Meanwhile, it is also possible to apply specific intensity distribution into the luminous flux of the reference light based on (Formula 3). FIGS. 15A to 15E are schematic diagrams illustrating the reference light having step-like intensity distribution within the luminous flux. An area in which intensity of the reference light is zero is schematically illustrated by a black area in the drawing. As illustrated in FIG. 6, the reflected light from the spherical body imitating the cell nucleus is characterized by being distributed locally in a partial area on the aperture of the detection lens. In FIGS. 15A to 15E, in response to this fact, it is illustrated that the reference light is distributed in a part of the detection lens. By using such reference light, the detection signal based on the reflected light from the living tissue can be relatively emphasized and then obtained. FIG. 15D is effective in specifically emphasizing an outer peripheral side of the detection lens. In other words, it is effective in emphasizing the light reflected at a large angle from the observation object. For example, it is effective in obtaining the detection signal while emphasizing a small structure within the living cell. FIG. 15E is effective in specifically emphasizing a middle peripheral area of the detection lens. In other words, it is effective in obtaining the detection signal while emphasizing the reflected light from a somewhat larger structure than that illustrated in FIG. 15D. These effects are generally referred to as the optical super-resolution, and can be obtained by applying not only the intensity distribution described herein but also similar phase distribution, which can be selected appropriately according to usage.

Figure 21:
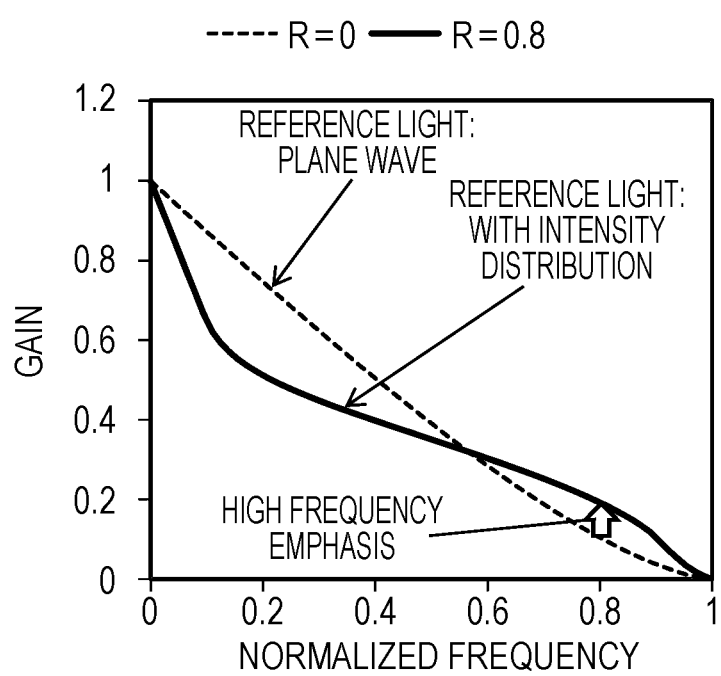
FIG. 21 is a result of calculating an OTF by the reference light according to an embodiment of the present invention.

FIG. 21 is an example of the optical super-resolution illustrating a result of calculating an optical transfer function (OTF) that indicates optical resolution when the intensity distribution illustrated in FIG. 15D is applied to the reference light. In the calculation, intensity of 80% or less of a luminous flux diameter is regarded as zero. As illustrated in the drawing, by applying the intensity distribution to the reference light, signal intensity in a high frequency side can be increased, and signal intensity in a low frequency side can be reduced. As a result, the observation object of an especially small size can be observed brightly. The optical super-resolution is generally a technique to improve the resolution by applying the intensity or phase distribution to the light radiated to the observation object. It has been proved herein, however, that the resolution can also be improved by applying the intensity or phase distribution to the reference light in a measurement system such as the OCT that causes the signal light and the reference light to interfere with each other. Especially, a living body measurement system should be controlled strictly by placing a limit on light energy allowed to be radiated to the observation object in consideration of safety. The conventional method, which changes the intensity or phase distribution of the light to be radiated to the observation object, causes a problem that a total amount of the light energy to be radiated or maximum power of the light energy at the focus is changed. By applying the phase or intensity distribution to the reference light according to an embodiment of the present invention, the light to be radiated to the observation object becomes constant. Therefore, it can be said that the technique according to an embodiment of the present invention is superior even from a safety point of view. Although the example described herein has referred to the case where the intensity distribution is applied into the luminous flux of the reference light, it is well known that a similar effect can be obtained by applying the phase distribution into the luminous flux.

Figure 16:
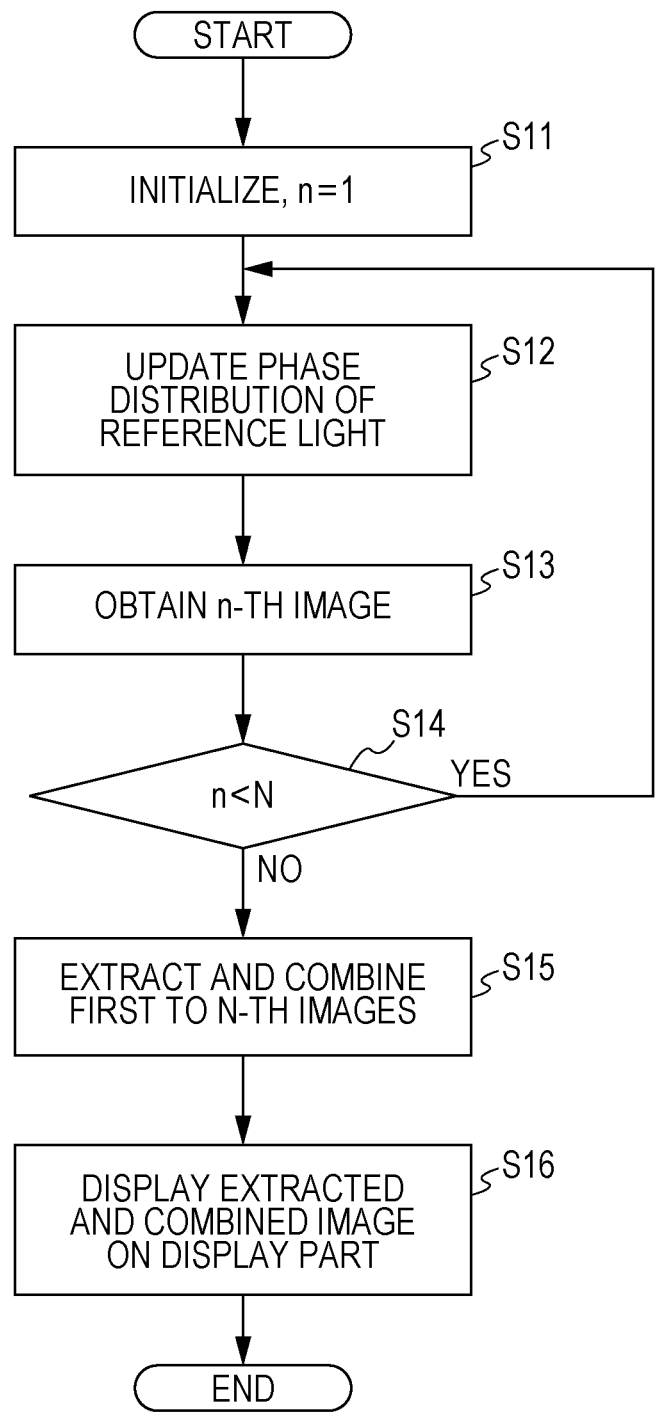
FIG. 16 is a flowchart illustrating a method for observing a plurality of items of image information by using the reference light having different phase distribution within the luminous flux, and combining the plurality of items of image information into an image to be displayed.

FIG. 16 is a flowchart illustrating the optical measurement method according to an embodiment of the present invention for observing a plurality of image information by using the reference light having different phase distribution within the luminous flux, and combining the plurality of image information into an image to be displayed. In the illustrated flowchart, the images are obtained N times. First, an apparatus and a measurement condition are initialized (S11). Determined phase distribution is applied into the luminous flux of the reference light (S12). The focus of the objective lens is scanned under the condition for the reference light to obtain an image from the detection signal (S13). These operations are repeated N times (S14). The obtained N images are appropriately extracted, combined (S15), and displayed (S16). Specifically, the following ways are effective for the present method. (1) Six kinds of phase distribution dependent on the radius illustrated in FIG. 10 are used to obtain N=6. A sharp image which has, for example, the largest contrast ratio is extracted for display by processing the obtained images. (2) Four kinds of phase distribution dependent on the radius illustrated in FIGS. 13A to 13D are used to obtain N=4. The obtained images are averaged and combined for display. (3) The conical phase distribution illustrated in FIG. 8B and the step-like phase distribution illustrated in FIG. 14B are selected to obtain N=2. A shape of the living tissue such as the cell nucleus is determined based on the image obtained by the step-like phase distribution. A central part of the image, namely an area with a small detection signal is replaced by the image obtained by the conical phase distribution, thereby producing a combined image for display. (4) A plurality of reference light beams with annular intensity distribution illustrated schematically in FIG. 15E is used to obtain images. The images are combined for display by extracting a focused component within the living cell or by emphasizing a predetermined plurality of structures.

Figure 19A:
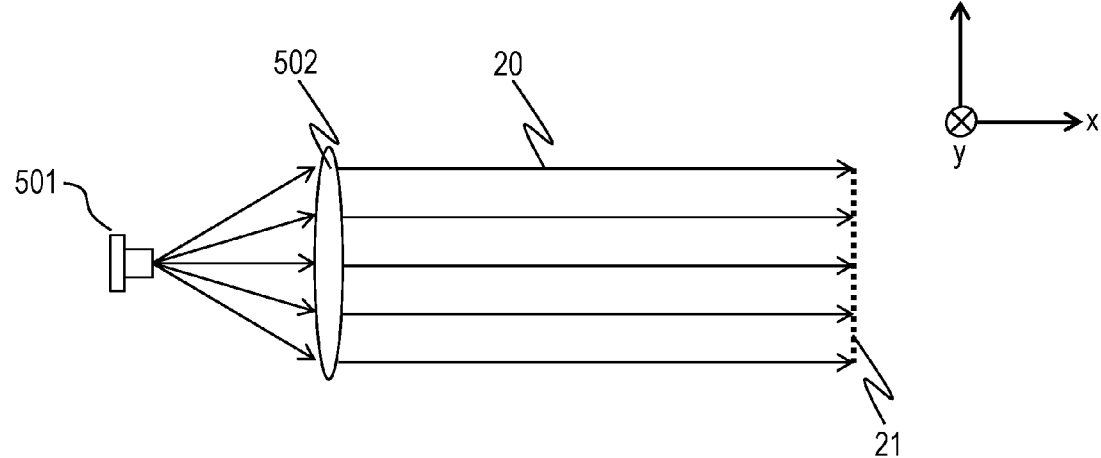
FIGS. 19A and 19B are diagrams schematically illustrating a difference between the reference light according to an embodiment of the present invention and the conventional reference light.
Figure 19B:
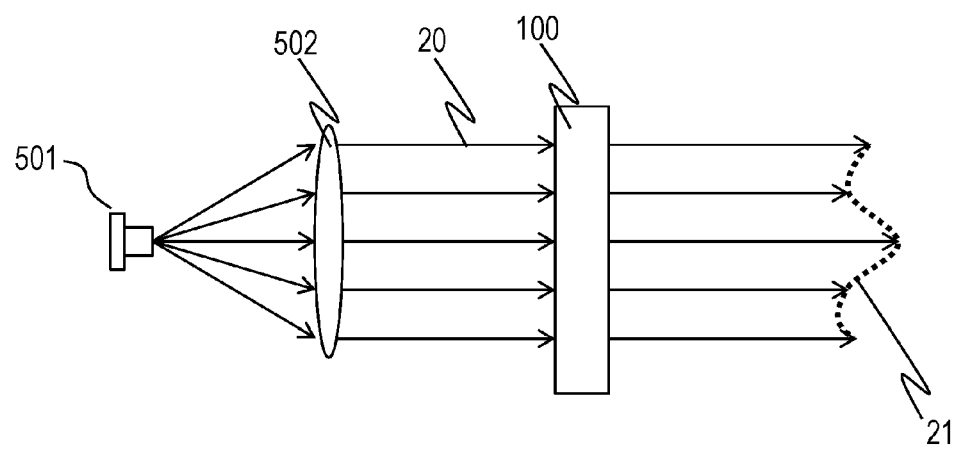

FIGS. 19A and 19B are diagrams schematically illustrating a difference between the reference light according to an embodiment of the present invention and the conventional reference light. FIG. 19A is a schematic diagram illustrating the conventional plane wave reference light. Laser light emitted from a light source 501 is converted to parallel light 20 by a collimate lens 502. The actual reference light is used by separating a portion of the luminous flux. As illustrated in the drawing, an equiphase surface 21 within the luminous flux is flat and does not have the phase distribution within the luminous flux. On the other hand, FIG. 19B is a schematic diagram illustrating the reference light according to an embodiment of the present invention. In the same way as the above, the laser light emitted from the light source 501 is converted to the parallel light 20 by the collimate lens 502. The parallel light 20 passes through an optical element 100 to apply the phase distribution into the luminous flux. The equiphase surface 21 thus has the nonuniform distribution within the luminous flux. As the optical element 100 for controlling the phase distribution within the luminous flux of the reference light, a transmissive optical element has been illustrated herein. The optical element 100, however, is not limited to the transmissive optical element, and a reflective optical element can also be used as the optical element 100.

Figure 17A:
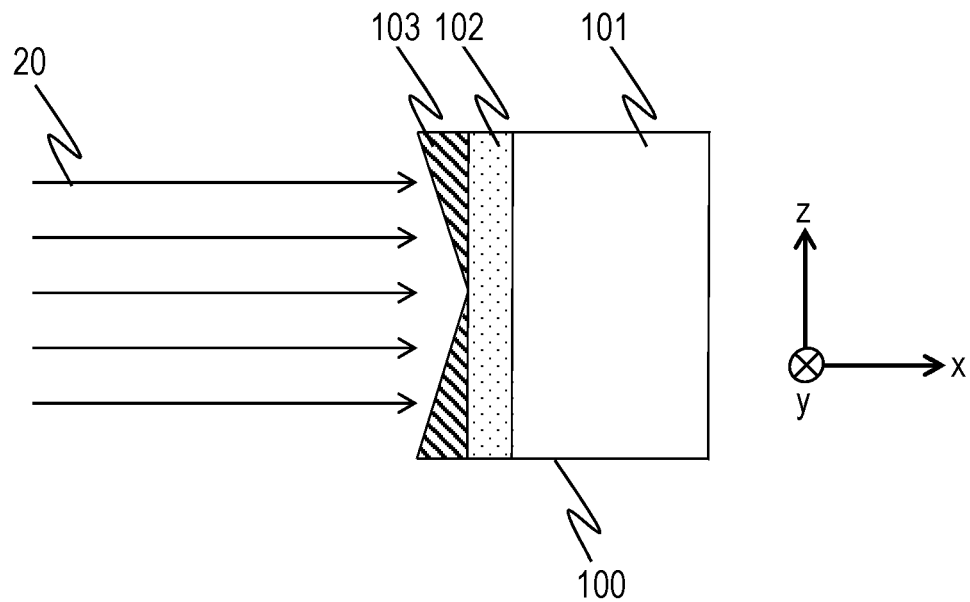
FIGS. 17A and 17B are schematic diagrams illustrating a reflective optical element that applies the phase distribution into the luminous flux of the reference light.
Figure 17B:
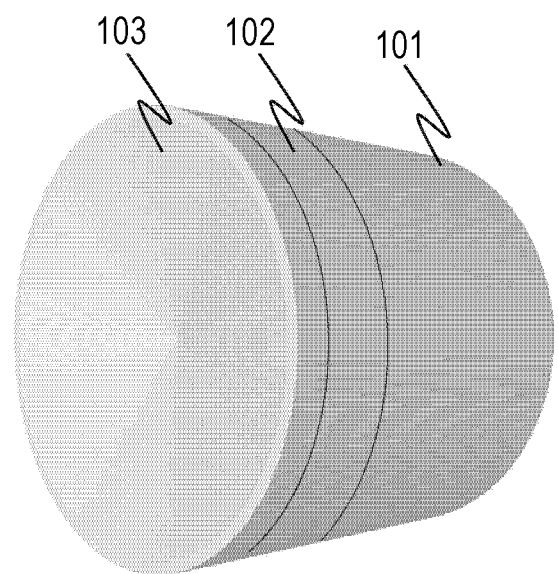

FIGS. 17A and 17B are schematic diagrams illustrating the reflective optical element that applies the phase distribution into the luminous flux of the reference light. A reflective optical element 100 in the drawing is processed such that a metal reflection layer 102 and a transparent dielectric layer 103 are accumulated in order on a substrate 101, and an etching technique or a nano-imprinting technique for a semiconductor process is used such that the dielectric layer 103 has specific thickness distribution. When the parallel light 20 is radiated to such a reflective optical element 100, the phase distribution is applied to the reflected reference light according to the thickness distribution of the transparent dielectric layer 103. An overview of this element is illustrated in FIG. 17B. This element has a surface shape as a function of the radius, thereby capable of applying the phase distribution illustrated in FIG. 10 to the reference light.

Figure 1:
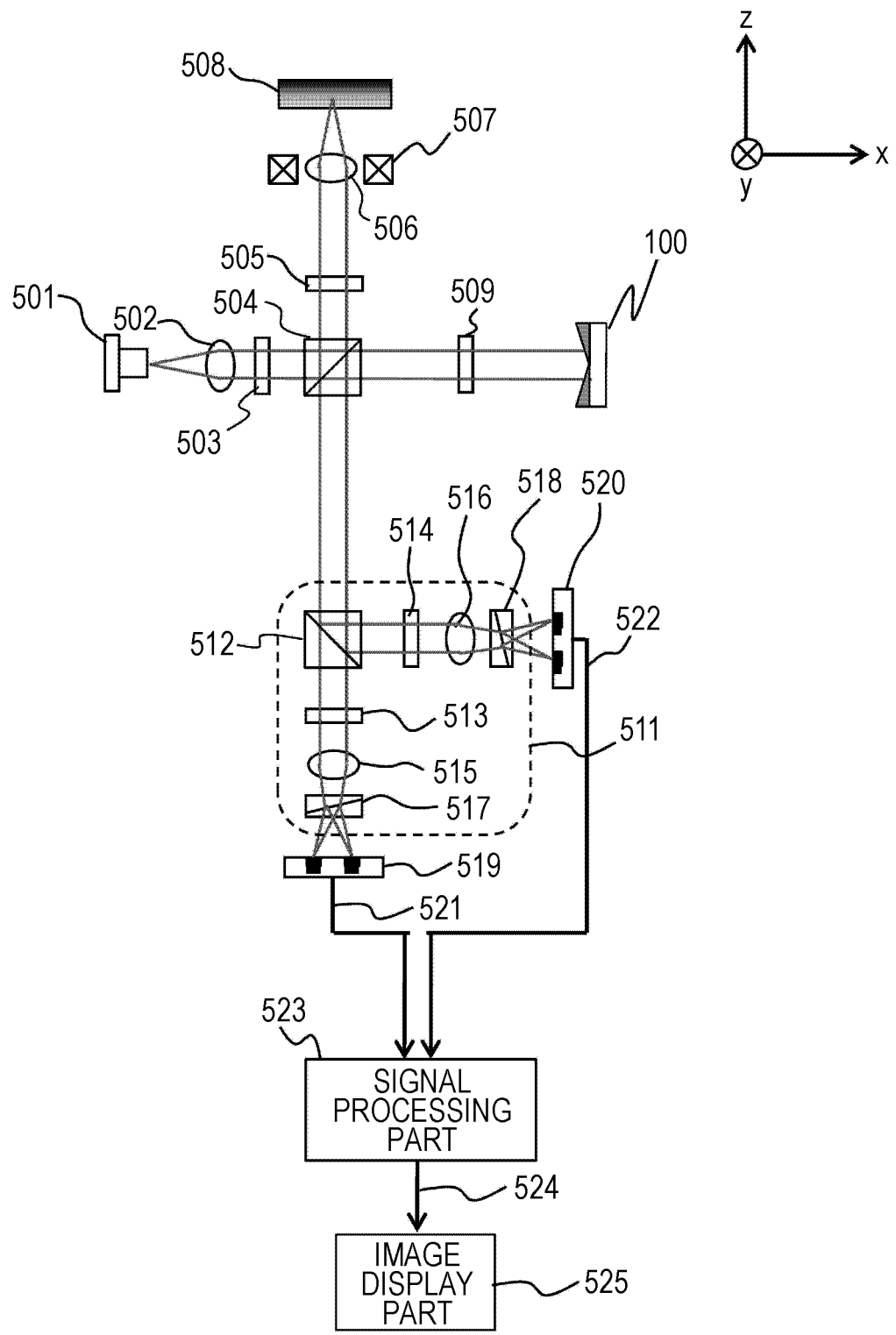
FIG. 1 is a schematic diagram illustrating an OCT apparatus configuration according to an embodiment of the present invention.
Figure 2:
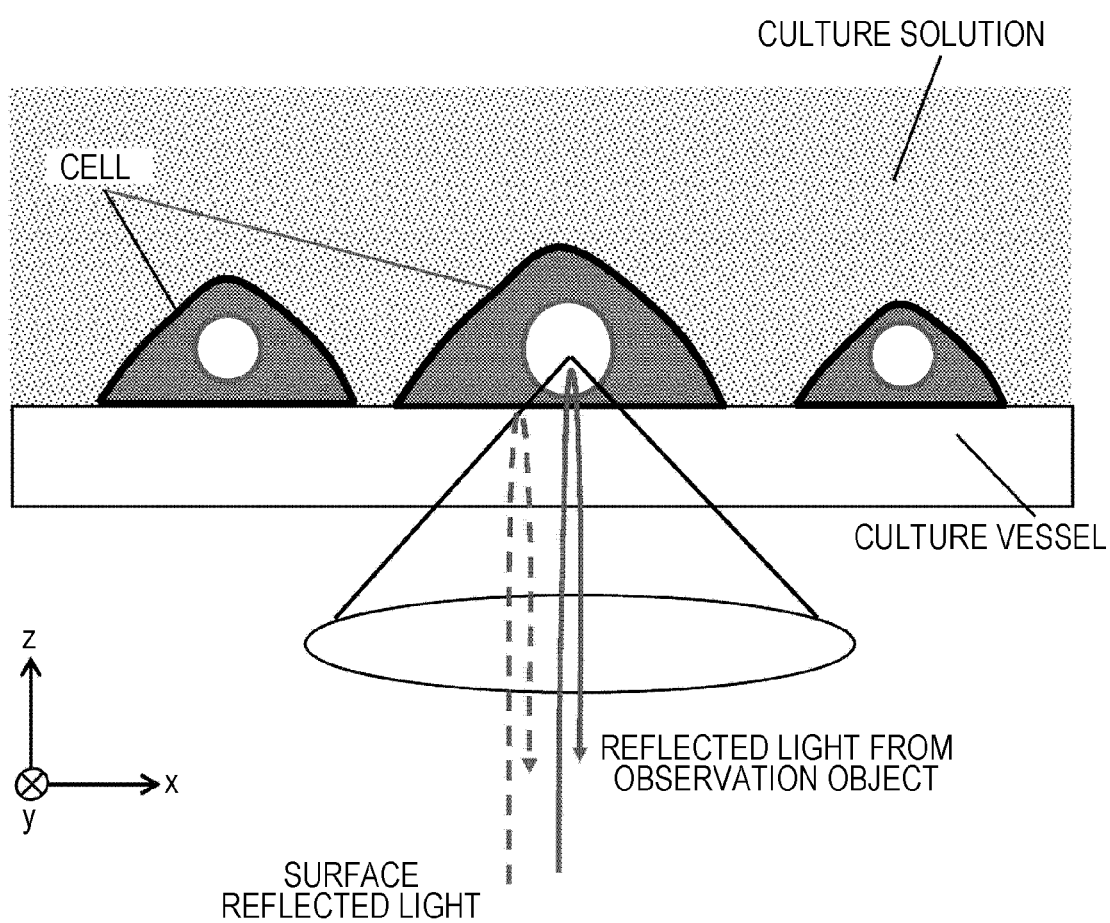
FIG. 2 is a schematic diagram illustrating signal light measured in the OCT apparatus.
Figure 3:
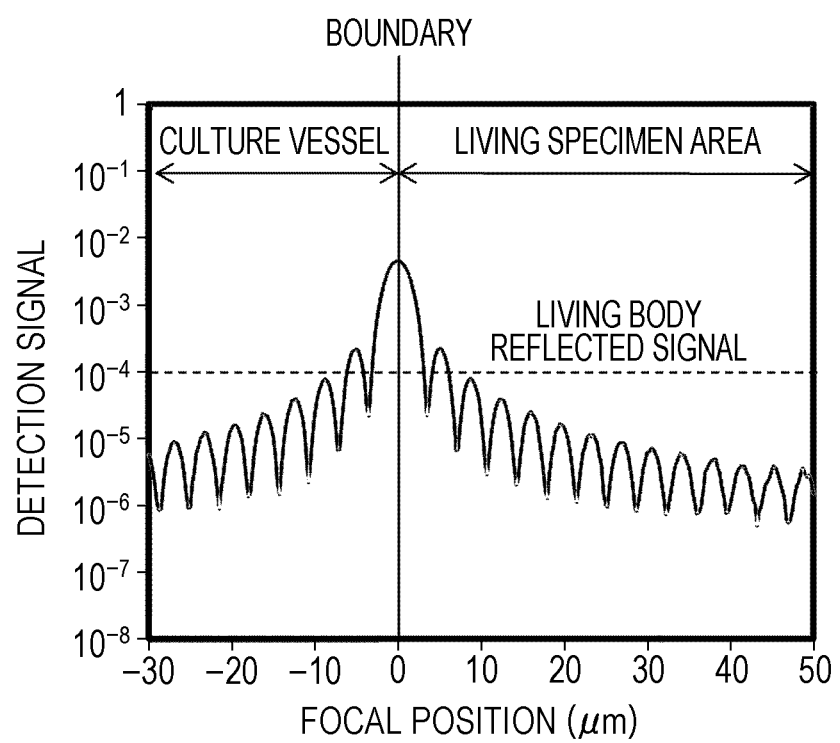
FIG. 3 is a result of calculating a detection signal by boundary reflection.
Figure 4A:
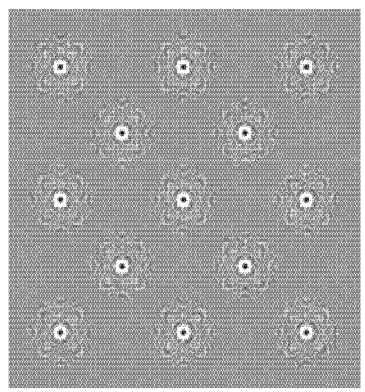
FIGS. 4A and 4B are diagrams comparing a simulation result and a measurement result by the OCT apparatus with respect to an X-Y image.
Figure 4B:
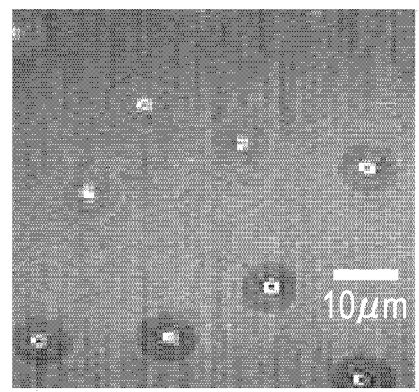

FIG. 1 is a schematic diagram illustrating a basic embodiment of an optical measurement apparatus according to an embodiment of the present invention. In the drawing, the laser light emitted from the light source 501 is converted to the parallel light by the collimate lens 502. Its polarization is then rotated by a λ/2 plate 503 which can adjust the optical axis direction. The parallel light is then branched into the signal light and the reference light by a polarizing beam splitter 504. The signal light reflected by the polarizing beam splitter 504 passes through a λ/4 plate 505, the optical axis direction of which has been set at about 22.5° with respect to the horizontal direction, whereby a polarization state is converted from s-polarization to circular polarization. After that, the signal light is collected by an objective lens 506 and radiated to an observation object 508. The objective lens 506 can perform the scan in the x-z direction by controlling a current amount to be supplied to a voice coil objective lens actuator 507. The observation object 508 can be moved in the y direction by a movable stage which is not illustrated in the drawing. Owing to such a configuration, the observation object can be scanned by changing the focal position of the objective lens in the x-y-z direction. The signal light reflected by the observation object passes through the objective lens 506. The polarization state is converted by the λ/4 plate 505 from the circular polarization to p-polarization. The signal light then enters the polarizing beam splitter 504. On the other hand, the reference light passes through a λ/4 plate 509. A polarization state is converted from p-polarization to circular polarization. The reference light then enters the reflective optical element 100 and is reflected by the reflective optical element 100. The phase or intensity distribution is applied into the luminous flux of the reference light. After that, the polarization state is converted by the λ/4 plate 509 from the circular polarization to s-polarization. The reference light then enters the polarizing beam splitter 504. The signal light and the reference light are combined by the polarizing beam splitter 504, whereby composite light is generated. The composite light is introduced to an interference optical system 511 including an half beam splitter 512, a λ/2 plate 513, a λ/4 plate 514, condenser lenses 515, 516, and Wollaston prisms 517, 518. The composite light enters the interference optical system 511 and is branched into transmitted light and reflected light by the half beam splitter 512. The transmitted light passes through the λ/2 plate 513, the optical axis of which has been set at about 22.5° with respect to the horizontal direction. The transmitted light is then collected by the condenser lens 515. The transmitted light is then polarized and separated by the Wollaston prism 517, whereby first interference light and second interference light are generated. A phase relation between the first interference light and the second interference light is different by 180 degrees. The first interference light and the second interference light are detected by a current differential type optical detector 519. Then, a differential output signal 521 proportional to a difference in the intensity between the first interference light and the second interference light is output. On the other hand, the reflected light passes through the λ/4 plate 514, the optical axis of which has been set at about 45 degrees with respect to the horizontal direction. The reflected light is then collected by the condenser lens 516. The reflected light is then polarized and separated by the Wollaston prism 518, whereby third interference light and fourth interference light are generated. A phase relation between the third interference light and the fourth interference light is different by about 180 degrees. The phase of the third interference light is different by about 90 degrees from the phase of the first interference light. The third interference light and the fourth interference light are detected by a current differential type optical detector 520. Then, a differential output signal 522 proportional to a difference in the intensity between the third interference light and the fourth interference light is output. The differential output signals 521, 522 (hereinafter referred to as I, Q) thus generated are input to a signal processing part 523 and undergo operation processing. A tomographic image of the observation object is formed based on an imaging signal 524 and displayed on an image display part 525. An imaginary aperture 150 in the drawing indicates an incorporeal, imaginary aperture of the detection lens obtained by projecting apertures of the condenser lenses 515 and 516 on the luminous flux of the signal light and reference light combined by the polarizing beam splitter 504. The imaginary aperture 150 is equivalent to the above-mentioned aperture of the detection lens.

A so-called phase diversity detection method described in "US 2014/0204388" is implemented in an operating principle of the interference optical system 511. The differential signals I and Q are expressed by the following forms, the details of which will be omitted in order to simplify the description.

[Mathematical formula 9]

$$I = \iint_A |E_{sig}(x, y)||E_{ref}(x, y)|\cos(\phi_{sig} - \phi_{ref})dxdy \quad (9)$$

[Mathematical formula 10]

$$Q = \iint_A |E_{sig}(x, y)||E_{ref}(x, y)|\sin(\phi_{sig} - \phi_{ref})dxdy \quad (10)$$

In the formulas, x, y represent a position on the imaginary aperture 150, $E_{sig}$ represents complex electric field amplitude of the signal light reflected from the observation object 508, $E_{ref}$ represents complex electric field amplitude of the reference light, $\varphi_{sig}$ represents a phase of the signal light corresponding to a light path length from the light source 501 to the imaginary aperture 150, and $\varphi_{ref}$ represents a phase of the reference light corresponding to a light path length from the light source 501 to the imaginary aperture 150. Correlation integral on the imaginary aperture 150 between the signal light and the reference light is meant by the integral.

By using these formulas, a detection signal S can be obtained by the following formula without depending on $\varphi_{sig}$ and $\varphi_{ref}$.

[Mathematical formula 11]

$$S = |E_{sig}|^2|E_{ref}|^2 = I^2 + Q^2 \quad (2)$$

Needless to say, (Formula 11) is equivalent to (Formula 3).

Figure 20:
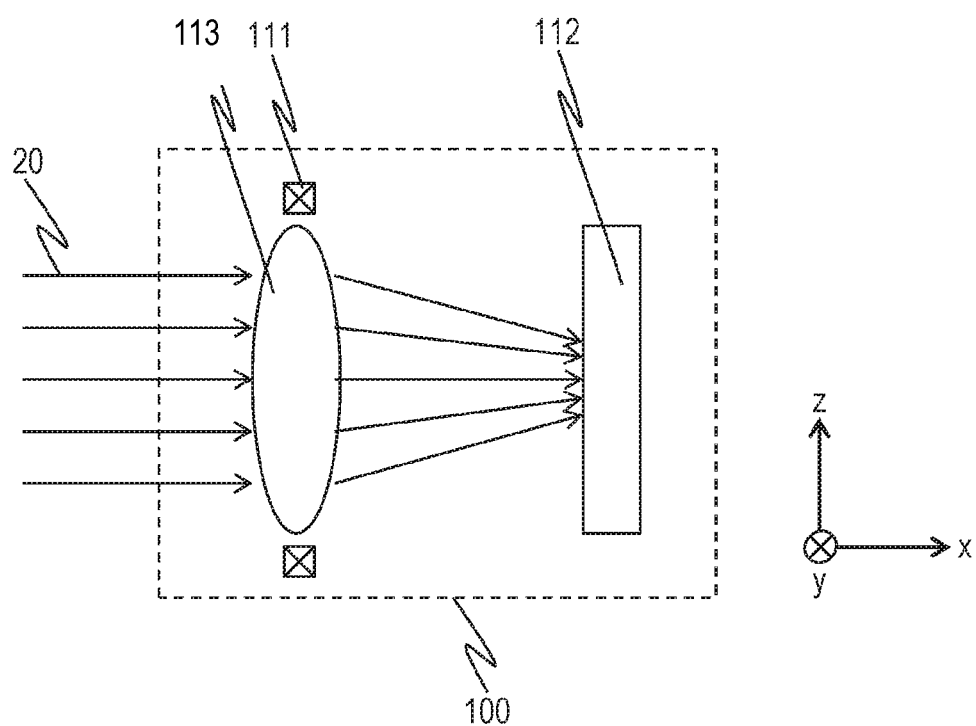
FIG. 20 is a schematic diagram illustrating a reflective optical element that applies the phase distribution proportional to the square of the radius into the luminous flux of the reference light.

In the present example, a high-quality measurement result can be obtained by measuring the living specimen using the reflective optical element 100 illustrated in FIGS. 17A and 17B or FIG. 20.

Figure 26:
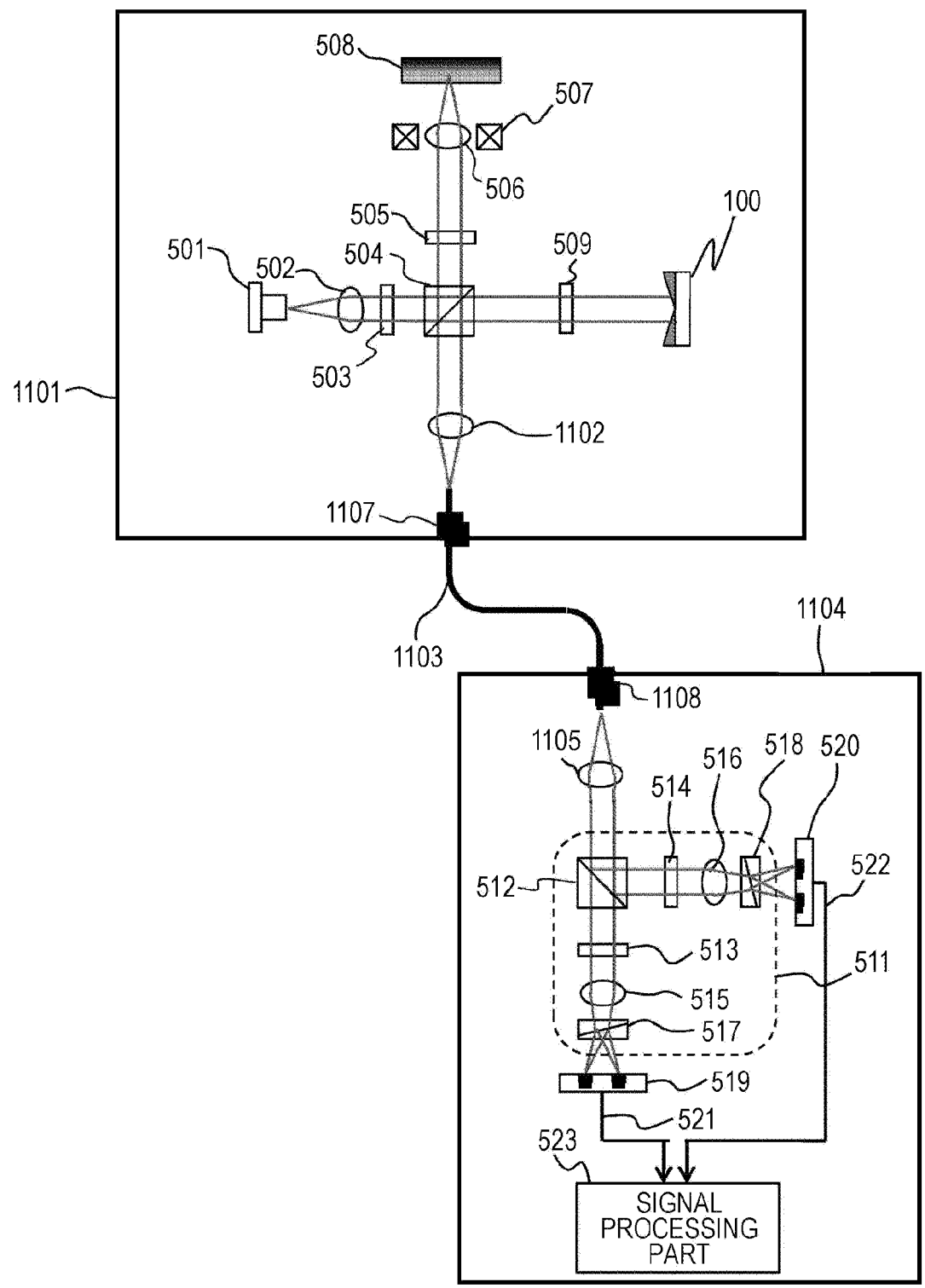
FIG. 26 is another example illustrating an OCT apparatus configuration according to an embodiment of the present invention.

FIG. 26 is an example in which the configuration shown in FIG. 1 has been separated into a signal measurement part 1101 and a detection system 1104 that are coupled to each other via a first lens 1102, optical fibers 1107, 1103, and 1108 and a second lens 1105. This example is suitable for downsizing the signal measurement part 1101 and making the signal measurement part 1101 movable.

Example 2

In Example 1, the optical detection method according to an embodiment of the present invention has been described, in which the predetermined (constant) phase distribution or intensity distribution is applied into the light path of the reference light. Hereinafter, another example will be described, in which a plurality of phase distribution or intensity distribution is used.

Figure 18:
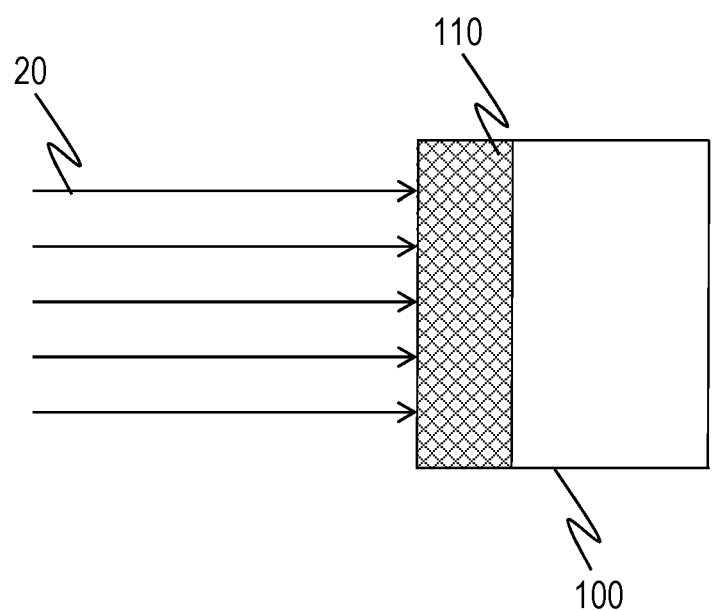
FIG. 18 is a schematic diagram illustrating a configuration of a reflective spatial phase modulator for forming arbitrary phase distribution within the luminous flux of the reference light.

FIG. 18 is a schematic diagram illustrating a reflective optical element for forming arbitrary phase distribution within the luminous flux of the reference light. A reflective optical element 100 includes a reflective phase applying element 110 which is formed in a two-dimensional array shape on a substrate. A spatial light modulator using a liquid crystal matrix can be used as such an array-like reflective phase applying element. By using such a reflective optical element 100, arbitrary phase distribution can be applied into the luminous flux when the reference light is reflected based on an array-like control signal which is not illustrated in the drawing.

FIG. 20 is a schematic diagram illustrating a reflective optical element that applies the phase distribution proportional to the square of the radius into the luminous flux of the reference light. In the drawing, a reflective optical element 100 includes a lens 113, an actuator 111, and a mirror 112. In this element, the lens 113 is moved in the x direction by the actuator 111, whereby a defocused state of the reference light collected by the mirror 112 can be controlled. It is well known that the defocus wavefront aberration has the phase distribution proportional to the square of the radius. By using this knowledge, the defocus aberration can be applied to the reference light reflected by the mirror. Magnitude of the phase to be applied can be controlled proportionally to a moving amount of the actuator. Therefore, the reflective optical element capable of applying variable phase distribution to the reference light can be provided by utilizing inexpensive components instead of using the spatial phase modulator illustrated in FIG. 18.

Figure 22A:
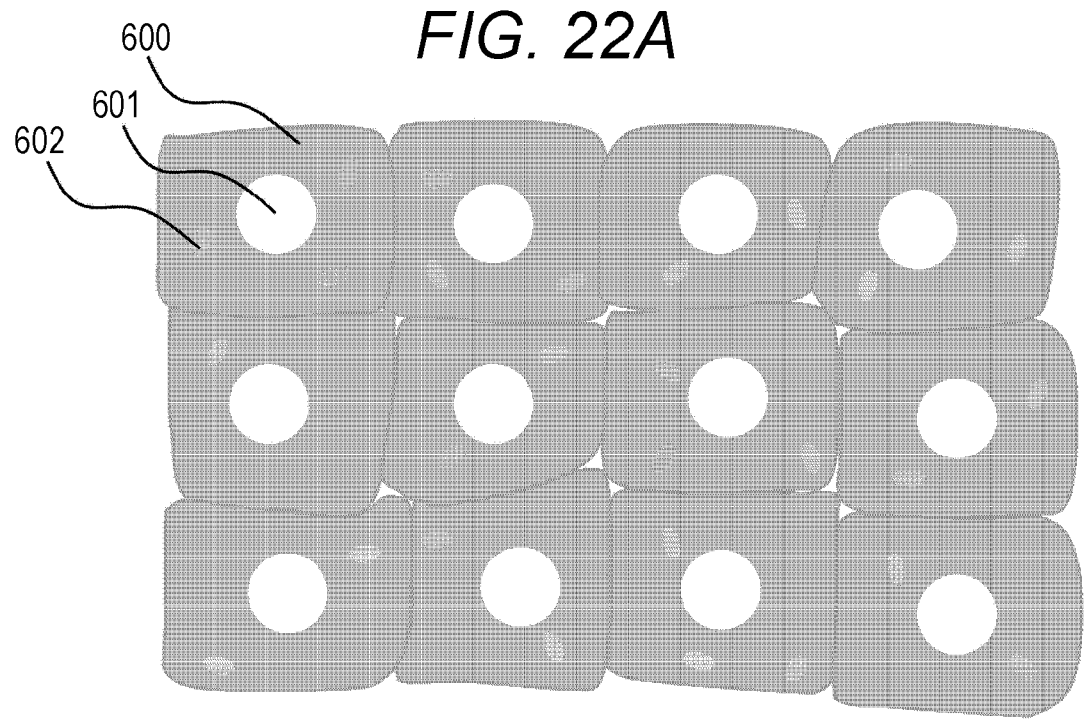
FIGS. 22A and 22B are schematic diagrams illustrating an observation image obtained in the x-y direction when the arbitrary phase distribution is applied into the luminous flux of the reference light.
Figure 22B:
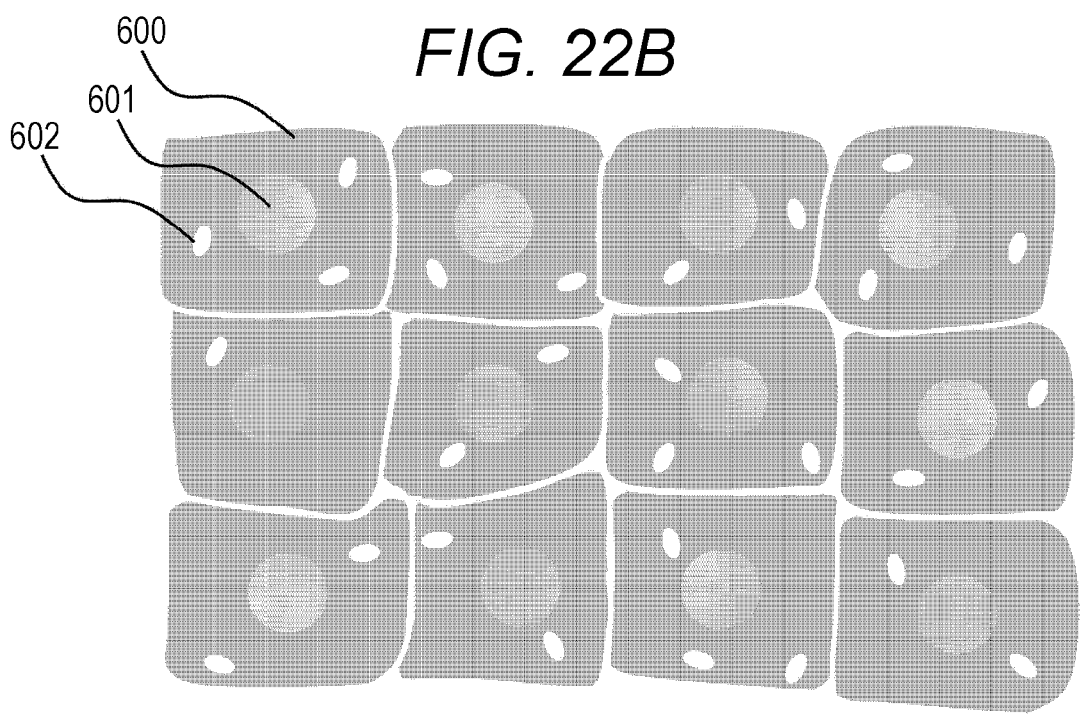

FIGS. 22A and 22B are schematic diagrams illustrating an observation image obtained in the x-y direction when the arbitrary phase distribution is applied into the luminous flux of the reference light. In the present invention, it is also effective to observe an object while changing the phase distribution to be applied into the luminous flux of the reference light by using the spatial light modulator or the like. FIG. 22A is a schematic diagram illustrating an x-y image of the living cell obtained under a normal condition. In the obtained image, luminance of a cell nucleus 601 positioned at a central part of each cell 600 is high. This is because that the size of the cell nucleus (about 10 μm) is greater than the wavelength of the light (approximately 0.4 to 2 μm), and a regular reflection component is greater than a diffuse reflection component. On the other hand, FIG. 22B is a schematic diagram illustrating an x-y image obtained by changing a condition of the spatial light modulator so as to increase spatial resolution of a light spot at the focus of the objective lens, and by emphasizing the reflected light from a finer component. As illustrated in the drawing, it is possible to obtain the image in which luminance of an organelle 602 (for example, a mitochondria and a Golgi body) is relatively higher than that of the cell nucleus 601.

Figure 23:
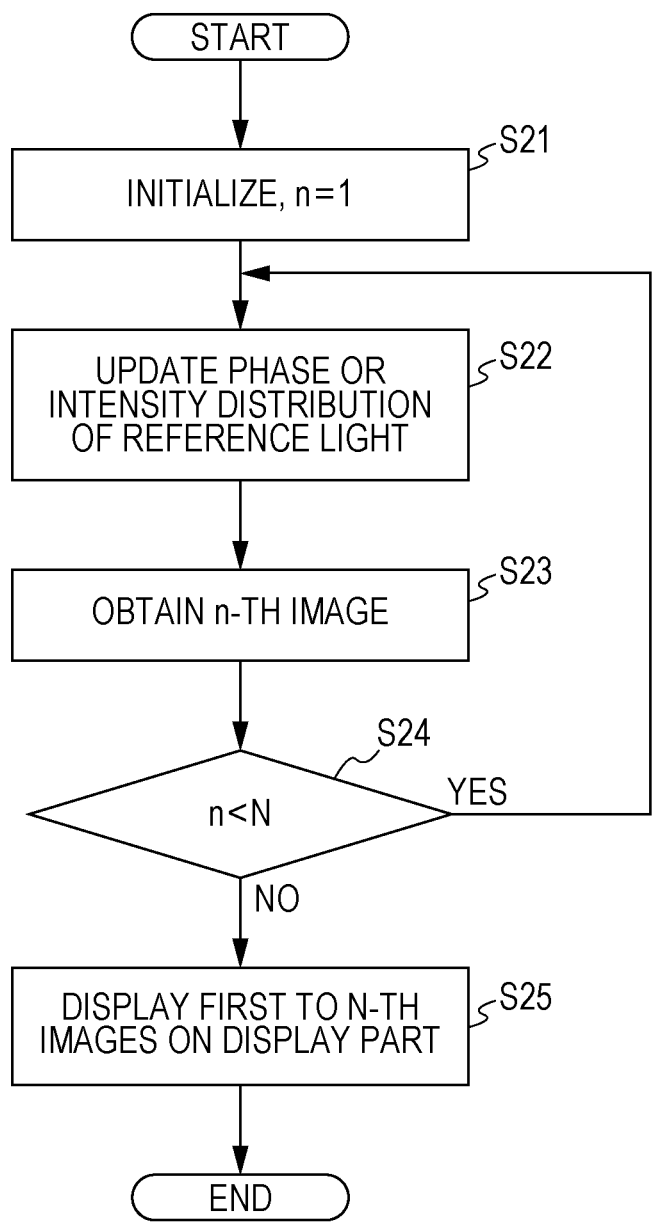
FIG. 23 is a flowchart illustrating an optical measurement method according to an embodiment of the present invention for obtaining a desired image by changing the intensity distribution or the phase distribution of the reference light.

FIG. 23 is a flowchart illustrating an optical measurement method according to an embodiment of the present invention for obtaining an image by changing the intensity distribution or the phase distribution of the reference light. In the illustrated flowchart, the images are obtained N times. First, an apparatus and a measurement condition are initialized (S21). Determined phase distribution is applied into the luminous flux of the reference light (S22). The focus of the objective lens is scanned under the condition for the reference light to obtain an image from the detection signal (S23). These operations are repeated N times (S24). The obtained N images are then displayed (S25). In the present method, a plurality of images illustrated in FIGS. 22A and 22B or the like can be automatically obtained. In order to obtain the image in which the organelle is emphasized as illustrated in FIG. 22B, an operator decides the best image among the obtained n images. The decided image is set as an initial condition, thereby supporting a parameter for applying the different phase or intensity distribution. The measurement is thus repeated to finally obtain the best image.

In the measurement apparatus of FIG. 1, a more adaptive measurement result can be obtained by measuring the living specimen using the reflective optical element 100 illustrated in FIG. 18.

In the present invention, as described above, the influence of the boundary reflection can be reduced by applying the phase distribution into the luminous flux of the reference light (FIGS. 8A and 8B). The measurement resolution can also be controlled by applying the intensity distribution into the luminous flux of the reference light (FIG. 21). These features can also be easily combined in the present invention. Specifically, by applying the phase distribution and the intensity distribution into the luminous flux of the reference light, the above-mentioned effects can be simultaneously obtained, and magnitude of the light signal to be detected can be controlled to a predetermined amount.

Example 3

The optical measurement apparatus illustrated in FIG. 1 has been described in Examples 1 and 2. Hereinafter, an exemplary configuration in which an entire optical system is driven will be described referring to FIG. 24.

Figure 24:
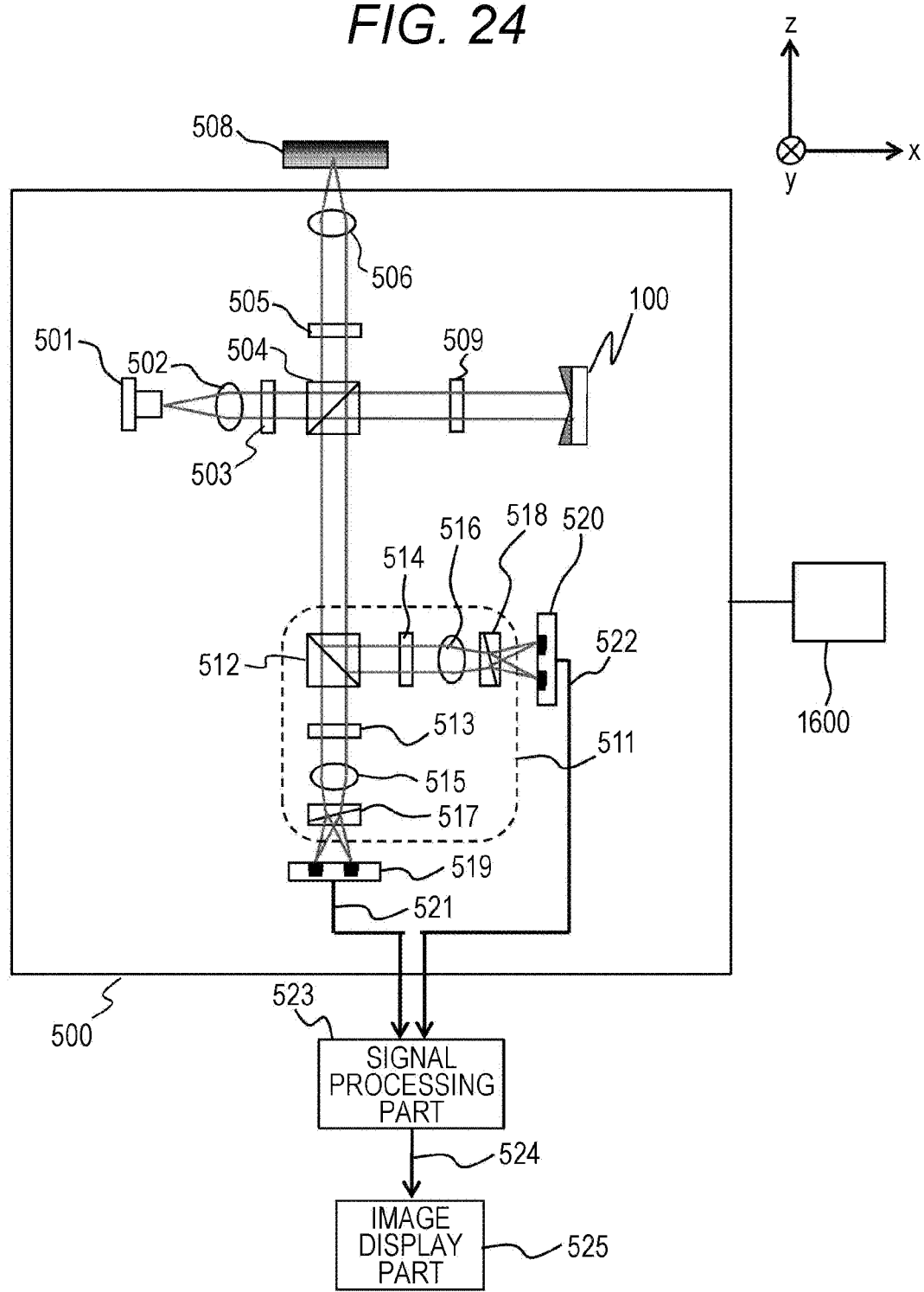
FIG. 24 is another example illustrating an OCT apparatus configuration according to an embodiment of the present invention.

FIG. 24 is another schematic diagram illustrating an optical measurement apparatus according to an embodiment of the present invention. In the present embodiment, a difference from the embodiment of FIG. 1 is that the measurement is performed by moving an optical system 500 by means of a stepping motor 1600 instead of using the actuator 507. The present example is inferior to the embodiment of FIG. 1 since a weight of a movable part and measurement time are increased. However, the present example is advantageous in that the optical system 500 is integrated to provide a high mechanical rigidity, and an internal light path length does not change, thereby capable of obtaining a high-quality image having a good S/N ratio.

The example in which the measurement is performed by moving the entire optical system 500 has been described herein. Meanwhile, the measurement can also be easily performed by fixing the optical system 500 while moving the observation object 508 by means of a similar stepping motor which is not illustrated in the drawing. In a case where the observation object is small and light, the latter method, which can reduce the measurement time, is superior to the other.

Example 4

The example in which phase diversity homodyne is used has been described in Example 1. The following description of the present example will refer to an example in which the technique according to an embodiment of the present invention is applied to a normal OCT apparatus.

Figure 25:
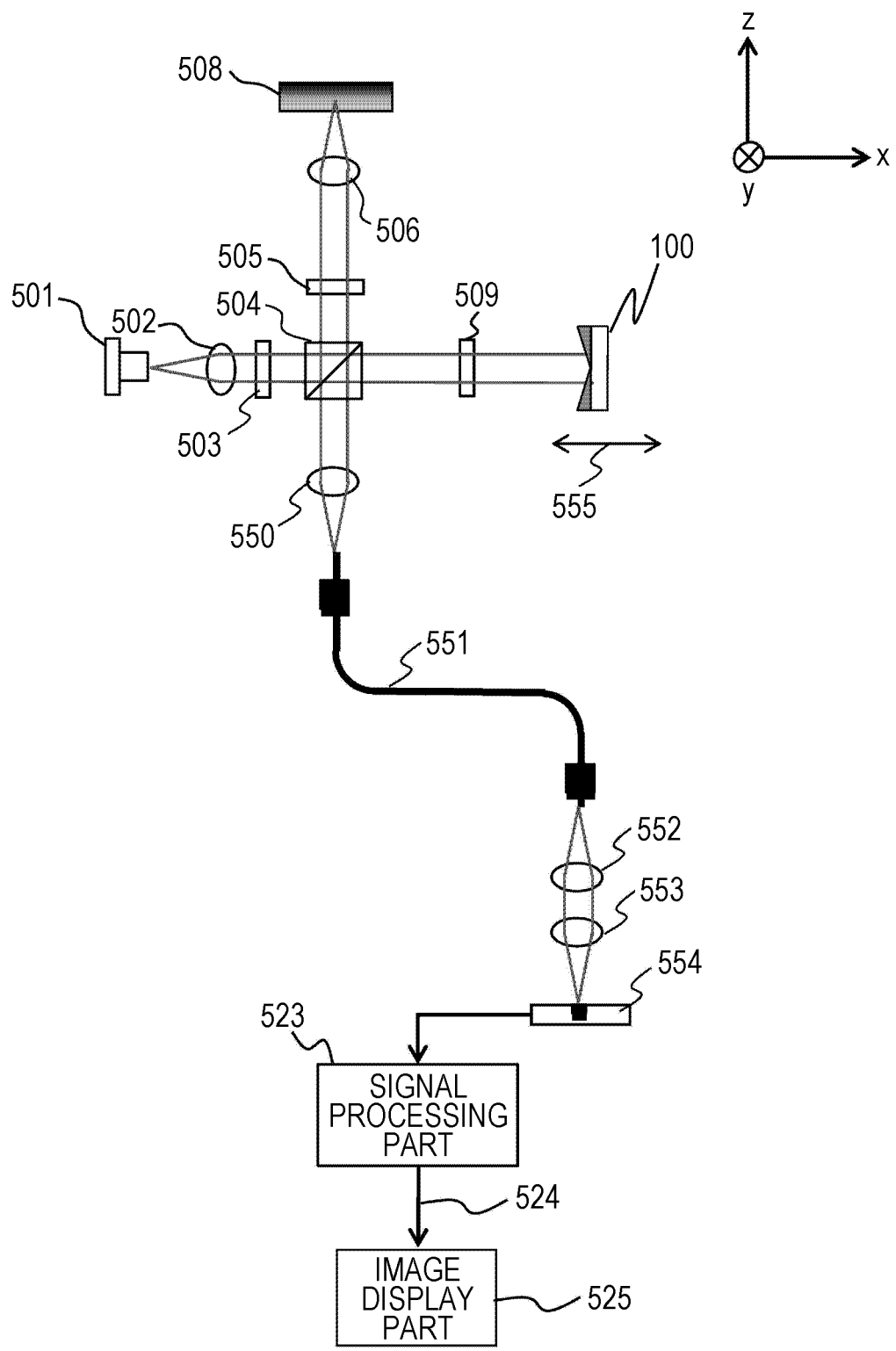
FIG. 25 is another example illustrating an OCT apparatus configuration according to an embodiment of the present invention.

FIG. 25 is another schematic diagram illustrating an optical measurement apparatus according to an embodiment of the present invention. In the present embodiment, a difference from the embodiment of FIG. 1 is that interference intensity between the signal light and the reference light is directly measured by means of lenses 550, 552, 553, an optical fiber 551, and an optical detector 554 instead of a phase diversity homodyne optical system, without using the actuator 507. In this configuration, a low-coherence light source such as an SLD, a coherence length of which is shorter than that of a laser, is used as the light source 501. A position of the reflective optical element 100 is adjusted along a moving direction 555 by a stepping motor which is not illustrated in the drawing, whereby the measurement is performed. In this case, when a difference in the light path length between the reflected light from the observation object 508 and the reference light is shorter than a predetermined length on the optical detector 554, such a component of the reflected light is emphasized by the interference. An interference signal is converted to an electrical signal in the optical detector 554. The electrical signal then undergoes envelope detection processing in the signal processing part 523, whereby the measurement can be performed. Phase information of the reflected light from the observation object cannot be obtained in this configuration since the phase diversity homodyne method is not used. This configuration is advantageous, however, for simplifying the configuration of the optical system, thereby reducing a cost of the apparatus.

The present invention is not limited to the above-mentioned examples, and includes a variety of modifications. For example, although the above-mentioned examples have been explained in detail for an easy understanding of the present invention, the present invention is not necessarily limited to what is provided with all of the described configurations. In addition, one example configuration can be partially replaced by another example configuration, and can be supplemented by another example configuration. Each example configuration can be partially deleted, or can be supplemented by/exchanged for another configuration.

What is claimed is:

1. An optical measurement apparatus comprising:
a light source configured to emit laser light;
an optical splitter configured to branch the laser light emitted from the light source into signal light and reference light;
an objective lens configured to collect the signal light to an observation object;
an optical element configured to apply at least one of a predetermined phase distribution or intensity distribution in a cross-section of the reference light vertical to a traveling direction of the reference light which modifies the phase distribution or the intensity distribution in the cross-section of the reference light;
an optical system configured to receive a unitary interference light beam which is generated by the optical splitter by combining the signal light reflected by the observation object with the reference light from the optical element and to generate a plurality of interference light beams having from the unitary interference light beam, the plurality of interference light beams having different phases;
a pair of detectors configured to detect the plurality of interference light beams from the optical splitter and which is generated by the optical splitter by combining the signal light reflected by the observation object with the reference light from the optical element;
a computer programmed to generate a tomographic image of the observation object based on a plurality of signals from the pair of detectors corresponding to the detected interference light beams,
wherein the tomographic image is obtained using a single intensity or phase distribution of the reference light.

2. The optical measurement apparatus according to claim 1, wherein the optical element is configured to apply a conical phase distribution.

3. The optical measurement apparatus according to claim 1, wherein the optical element is configured to apply a phase distribution expressed by:

$$E_{ref}(x, y, z_0) = A\exp\left(i\Phi_0 \frac{\sqrt{x^2+y^2}}{R}\right)\exp\left(i\frac{2\pi}{\lambda}L\right)$$

wherein $\varphi_0$ is a maximum value of a phase to be applied, R is a radius of an aperture of a detection lens, $(2\pi/\lambda)L$ is a phase based on a light path length of the reference light, x, y, and $z_0$ are respective points on the aperture of the detection lens, and A represents an amplitude.

4. The optical measurement apparatus according to claim 1, wherein the optical element is configured to apply a phase distribution expressed by:

$$E_{ref}(x, y, z_0) = A\exp(i\Phi_0 r^a)\exp\left(i\frac{2\pi}{\lambda}L\right)$$

wherein $\varphi_0$ is a maximum value of a phase to be applied, $(2\pi/\lambda)L$ is a phase based on a light path length of the reference light, A is amplitude, a is a degree having values of a=0, 0.5, 1, 2, 3, and 4, and r is a normalized radius determined by a position (x, y, $z_0$) within the aperture of the detection lens and the radius R of the aperture of the detection lens.

5. The optical measurement apparatus according to claim 1, wherein the optical element is configured to apply a stepped phase distribution.

6. The optical measurement apparatus according to claim 5, wherein the element is configured to divide the cross section of the reference light into an inner peripheral side and an outer peripheral side and to apply a phase difference to the inner peripheral side of the reference light.

7. The optical measurement apparatus according to claim 5, wherein, in the stepped phase distribution, an area in which a phase applied within an aperture of a detection lens is zero and an area in which a phase applied within the aperture of the detection lens is $\lambda/2$ are substantially equal in size.

8. The optical measurement apparatus according to claim 1, wherein the optical element is configured to apply a stepped intensity distribution.

9. The optical measurement apparatus according to claim 1, wherein the optical element is a spatial light modulator.

10. The optical measurement apparatus according to claim 1, wherein the optical element is configured to change a defocused state of the reference light.

11. The optical measurement apparatus according to claim 1, wherein the plurality of interference light beams is four beams of the interference light that have phase relations different from one another, and two of the four beams of the interference light are detected by each of one the detectors.

12. The optical measurement apparatus according to claim 1, further comprising:
a driving motor configured to integrally drive the light source, the optical splitter, the objective lens, the optical system, and the detector.

13. An optical measurement method comprising:
branching laser light into signal light and reference light;
collecting and radiating the signal light to an observation object having a three-dimensional shape via a boundary surface regarded as a plane surface;
applying at least one of a predetermined phase distribution or intensity distribution in a cross-section of the reference light vertical to a traveling direction of the reference light which modifies the phase distribution or the intensity distribution in the cross-section of the reference light;
causing the signal light reflected from the observation object and the reference light, in which at least one of the predetermined phase distribution or intensity distribution is applied, to interfere and generate interference light in order to generate a unitary interference light beam;
detecting the interference light;
generating a tomographic image of the observation object based on a detection signal of the detected unitary interference light beam,
wherein the tomographic image is obtained using a single intensity or phase distribution of the reference light.

14. The optical measurement method according to claim 13, wherein a combined tomographic image is produced by repeating a plurality of times:
applying the phase distribution to the reference light; and
obtaining the tomographic image from the detection signal of the interference light generated using the reference light to which the single intensity or phase distribution has been applied.

15. The optical measurement method according to claim 13, wherein the single intensity or phase distribution of the reference light is a conical phase distribution or a stepped phase distribution.

16. An optical measurement apparatus comprising:
a light source configured to emit low-coherence light;
an optical splitter configured to branch the light emitted from the light source into signal light and reference light;
an objective lens configured to collect the signal light to an observation object;
an optical element configured to apply at least one of a predetermined phase distribution or intensity distribution in a cross-section of a luminous flux of the reference light vertical to a traveling direction of the reference light which modifies the phase distribution or the intensity distribution in the cross-section of the reference light;
a detector configured to receive a unitary interference light beam from the optical splitter, the unitary interference light beam being generated by the optical splitter by combining the signal light reflected by the observation object and the reference light from the optical element, and to detect the unitary interference light beam;
a computer programmed to generate a tomographic image of the observation object based on a signal from the detector corresponding to the detected unitary interference light beam,
wherein the tomographic image is obtained using a single intensity or phase distribution of the reference light.

17. The optical measurement apparatus according to claim 16, wherein the optical element is configured to apply a conical phase distribution.

18. The optical measurement apparatus according to claim 16, wherein the optical element is configured to apply a stepped phase distribution, and
wherein the optical element is configured to divide the luminous flux of the reference light into an inner peripheral side and an outer peripheral side and to apply a phase difference to the inner peripheral side of the reference light.

19. The optical measurement apparatus according to claim 16, wherein the optical element is configured to apply a stepped phase distribution, and
wherein, in the stepped phase distribution, an area in which a phase applied within an aperture of a detection lens is zero and an area in which a phase applied within the aperture of the detection lens is $\lambda/2$ are substantially equal in size.

20. The optical measurement apparatus according to claim 16, further comprising:
a stepping motor configured to move the optical element in the traveling direction of the reference light,
wherein the optical element is a spatial light modulator.

* * * * *